United States Patent
Abdolahad et al.

(10) Patent No.: US 11,874,268 B2
(45) Date of Patent: Jan. 16, 2024

(54) METHOD AND SYSTEM FOR METASTASIS DIAGNOSIS AND PROGNOSIS

(71) Applicants: Mohammad Abdolahad, Tehran (IR); Mohammad Saeid Nik Shoar, Tehran (IR); Mahsa Faramarzpour Darzini, Tehran (IR)

(72) Inventors: Mohammad Abdolahad, Tehran (IR); Mohammad Saeid Nik Shoar, Tehran (IR); Mahsa Faramarzpour Darzini, Tehran (IR)

(73) Assignee: NANOHESGARSAZAN SALAMAT ARYA NCUBATION CENTER FOR EQUIPMENT AND DEVICES, Tehran (IR)

(*) Notice: Subject to any disclaimer, the term of this patent is extended or adjusted under 35 U.S.C. 154(b) by 810 days.

(21) Appl. No.: 17/006,791

(22) Filed: Aug. 29, 2020

(65) Prior Publication Data
US 2020/0393439 A1 Dec. 17, 2020

Related U.S. Application Data

(63) Continuation-in-part of application No. 15/616,054, filed on Jun. 7, 2017, now Pat. No. 10,761,081.
(Continued)

(51) Int. Cl.
*G01N 33/483* (2006.01)
*G01N 33/574* (2006.01)
(Continued)

(52) U.S. Cl.
CPC ....... *G01N 33/4836* (2013.01); *G01N 33/574* (2013.01); *C23C 14/185* (2013.01); *H01J 37/32082* (2013.01); *H01J 2237/3341* (2013.01)

(58) Field of Classification Search
None
See application file for complete search history.

(56) References Cited

U.S. PATENT DOCUMENTS 6,402,689 B1* 6/2002 Scarantino ......... A61B 5/14539
600/407
6,641,708 B1* 11/2003 Becker ............... G01N 30/0005
204/547

(Continued)

*Primary Examiner* — Brian R Gordon
(74) *Attorney, Agent, or Firm* — Bajwa IP Law Firm; Haris Zaheer Bajwa

(57) ABSTRACT

A method for fabricating a biosensor for metastasis diagnosis. The method includes coating a photoresist layer on a substrate layer, forming a patterned region by patterning the photoresist layer utilizing a photolithography process, forming a nano-roughened patterned region by forming a plurality of nano-features on the patterned region, stripping the photoresist layer from the substrate layer, forming an array of microelectrodes and a corresponding array of electrical connections on the nano-roughened patterned region by depositing a gold/titanium (Au/Ti) bilayer on the substrate layer with the nano-roughened patterned region and forming a metastatic cell sensing trap on at least one microelectrode of the array of microelectrodes. Where, forming the metastatic cell sensing trap includes placing a solution of Human Umbilical Vein Endothelial Cells (HUVECs) on the biosensor and forcing an attachment between at least one HUVEC of the HUVECs and the at least one microelectrode on the biosensor.

17 Claims, 35 Drawing Sheets

Related U.S. Application Data

(60) Provisional application No. 62/403,723, filed on Oct. 4, 2016, provisional application No. 62/348,953, filed on Jun. 12, 2016.

(51) Int. Cl.
*C23C 14/18* (2006.01)
*H01J 37/32* (2006.01)

(56) References Cited

U.S. PATENT DOCUMENTS

| | | | |
|---|---|---|---|
| 6,716,642 B1* | 4/2004 | Wu | B01J 19/0046 |
| | | | 435/68.1 |
| 6,858,439 B1* | 2/2005 | Xu | B01L 3/5025 |
| | | | 422/50 |
| 7,459,303 B2* | 12/2008 | Wang | G01N 33/5438 |
| | | | 435/297.5 |
| 7,470,533 B2* | 12/2008 | Xu | C12M 41/36 |
| | | | 435/288.2 |
| 10,154,592 B2* | 12/2018 | Rogers | H01L 21/31111 |
| 2002/0036142 A1* | 3/2002 | Gascoyne | B03C 5/028 |
| | | | 204/547 |
| 2003/0060695 A1* | 3/2003 | Connelly | A61M 1/3621 |
| | | | 600/365 |
| 2003/0114366 A1* | 6/2003 | Martin | A61K 38/17 |
| | | | 514/8.1 |
| 2005/0215764 A1* | 9/2005 | Tuszynski | C07K 14/435 |
| | | | 530/358 |
| 2005/0221270 A1* | 10/2005 | Connelly | A61B 5/415 |
| | | | 435/4 |
| 2005/0221271 A1* | 10/2005 | Murphy | B01L 3/50853 |
| | | | 435/4 |
| 2005/0249667 A1* | 11/2005 | Tuszynski | A61N 7/00 |
| | | | 424/9.3 |
| 2007/0178522 A1* | 8/2007 | Shiotsuka | C07K 16/44 |
| | | | 435/7.1 |
| 2008/0160539 A1* | 7/2008 | Murphy | B01L 3/5085 |
| | | | 435/7.1 |
| 2012/0142088 A1* | 6/2012 | Hsiao | C12N 5/0006 |
| | | | 435/325 |
| 2014/0024068 A1* | 1/2014 | Gratzl | G01N 33/5008 |
| | | | 435/287.1 |
| 2014/0315213 A1* | 10/2014 | Nagrath | B01L 3/5027 |
| | | | 435/7.1 |
| 2015/0285808 A1* | 10/2015 | Nagrath | G01N 33/54366 |
| | | | 435/7.23 |
| 2016/0050750 A1* | 2/2016 | Rogers | H05K 3/285 |
| | | | 361/767 |
| 2018/0066222 A1* | 3/2018 | Santra | A61N 1/325 |
| 2018/0066299 A1* | 3/2018 | Kim | C12M 23/12 |
| 2018/0103852 A1* | 4/2018 | Dagdeviren | A61B 5/442 |
| 2021/0255172 A1* | 8/2021 | Beskok | B01L 3/50273 |
| 2021/0270801 A1* | 9/2021 | Kim | G01N 33/4836 |
| 2022/0134131 A1* | 5/2022 | Bourke, Jr. | A61N 5/067 |
| | | | 607/88 |

* cited by examiner

METHOD AND SYSTEM FOR METASTASIS DIAGNOSIS AND PROGNOSIS

CROSS REFERENCE TO RELATED APPLICATION

This application is a continuation-in-part of U.S. patent application Ser. No. 15/616,054, now U.S. Pat. No. 10,761,081, filed Jun. 7, 2017, and entitled "METHOD AND SYSTEM FOR METASTASIS DIAGNOSIS AND PROGNOSIS", which takes priority from U.S. Provisional Patent Application Ser. No. 62/348,953 filed on Jun. 12, 2016, and entitled "ELECTRICAL INVASION ASSAY BASED ON NANO-ROUGHENED PMMA SUBSTRATE" and U.S. Provisional Patent Application Ser. No. 62/403,723 filed on Oct. 4, 2016, and entitled "AN OPTICAL-ELECTRICAL METHOD AND DEVICE FOR METASTASIS DIAGNOSIS", which are all incorporated herein by reference in their entirety.

TECHNICAL FIELD

The present application generally relates to the metastasis diagnosis and prognosis, using methods and systems based on the invasion tendency of metastatic cells to the Human Umbilical Vein Endothelial Cells (HUVECs).

BACKGROUND

Metastasis occurs when cancer cells acquire a migratory epithelial-to-mesenchymal transition (EMT) phenotype, initiated from groupings of cells that appear to break off from primary tumors. Invasive phenotype is the fundamental property of such cells in correlation with their invasion to endothelial vascular layer in the beginning of the metastasis. Identifying metastatic cancer cells in a sample resected from the secondary tissue of the patients by biopsy, core needle biopsy (CNB), endoscopy, colonoscopy, Lymph node aspiration, and fine needle aspiration (FNA) is the most important step in cancer staging and therapeutic regimes.

Accurate detection of the occurrence of metastasis in the samples removed by biopsy has a major impact on patients' survival rates. Existing pathological methods are designed to track the presence of abnormally aggressive cells in the fixed samples prepared from removed tissues by cytological and immunohistochemical staining procedures. The small volume of the biopsied tissue from the organs in question for metastasis results in limited number of histopathological samples investigated by pathologists and reduces rates of accurate diagnosis especially in early stages of metastasis. Current molecular technologies specifically negatively limit the ability to demonstrate metastasis in biopsy samples with low cellular population. Although cancer cells are detectable in some cases using traditional methods, they might be rare or only exist in regions of the removed sample that are not investigated by a pathologist, thereby leading to missing any aggressive cancer cells. Accordingly, to do a detailed analysis using traditional methods which doesn't miss any cancer cells is both time consuming and expensive.

Therefore, there is a need for an approach, a system, and a method to accurately detect the presence of metastasis in unprocessed samples for cancer diagnosis, prognosis, drug development, and cancer treatment applications. A chemistry-free approach may enable specific and label-free efficient capture of metastatic cells with a simple, fast, and chemistry free method in small biopsy samples which will improve the diagnostic impact of CNB before surgery or therapeutic treatments.

SUMMARY

In one general aspect of the present disclosure, an exemplary method for fabricating a biosensor for metastasis diagnosis is disclosed. The method may include coating a photoresist layer on a substrate layer, forming a patterned region by patterning the photoresist layer utilizing a photolithography process, forming a nano-roughened patterned region by forming a plurality of nano-features on the patterned region, stripping the photoresist layer from the substrate layer, forming an array of microelectrodes and an array of electrical connections respective to the array of microelectrodes on the nano-roughened patterned region by depositing a gold/titanium (Au/Ti) bilayer on the substrate layer with the nano-roughened patterned region and forming a metastatic cell sensing trap on each microelectrode of the array of microelectrodes. In an exemplary implementation, forming the metastatic cell sensing trap may include placing a solution of Human Umbilical Vein Endothelial Cells (HUVECs) on the biosensor and forcing an attachment between at least one HUVEC of the HUVECs and at least one microelectrode on the biosensor.

In an exemplary implementation, coating the photoresist layer on the substrate layer may include spin coating the photoresist layer on the substrate layer. In an exemplary implementation, coating the photoresist layer on the substrate layer may include coating the photoresist layer on the at least one of a Poly(methyl methacrylate) (PMMA) layer, and a glass layer.

In an exemplary implementation, forming the patterned region may include patterning the photoresist layer with a pattern including one of a regular pattern for arrangement of the array of microelectrodes and a non-regular pattern for arrangement of the array of microelectrodes. In an exemplary implementation, the regular pattern may include one of a parallel arrangement for the array of microelectrodes and a circular arrangement for the array of microelectrodes.

In an exemplary embodiment, the parallel arrangement for the array of microelectrodes may include a plurality of couple electrodes placed parallel to each other. In an exemplary embodiment, each couple electrodes may include a first electrode and a second electrode located at the bottom of the first electrode. In an exemplary embodiment, a distance between the first electrode and the second electrode may be less than 10 μm.

In an exemplary embodiment, the circular arrangement for the array of microelectrodes may include an electrical ground including a circular electrode at a center of the patterned region and a plurality of circular electrodes located around the electrical ground. In another exemplary embodiment, the circular arrangement for the array of microelectrodes may include a plurality of couple circular electrodes with a circular arrangement. In an exemplary embodiment, each couple electrodes may include a first circular electrode, and a second circular electrode located adjacent to the first electrode. In an exemplary embodiment, a distance between the first electrode and the second electrode is less than 10 μm.

In an exemplary implementation, forming the plurality of nano-features on the patterned region may include placing the substrate with the patterned region in a reactive ion etching (RIE) system and processing the patterned region with $SF_6$, $H_2$ and $O_2$ gases in the presence of radiofrequency (RF) Plasma. In an exemplary implementation, forming the plurality of nano-features on the patterned region may include forming a plurality of nano-sized hills on the patterned region with a width of less than 80 nm and a depth of less than 120 nm for each respective hill of the plurality of nano-sized hills.

In an exemplary implementation, depositing the bilayer of Au/Ti on the substrate layer with the plurality of nano-features on the patterned region may be carried out utilizing a sputtering process. In an exemplary implementation, depositing the Au/Ti bilayer on the substrate layer with the nano-roughened patterned region may include depositing a Ti layer with a thickness between 3 nm and 10 nm on the substrate layer with the nano-roughened patterned region utilizing a sputtering process and depositing an Au layer with a thickness between 10 nm and 50 nm on the deposited Ti layer utilizing a sputtering process.

In an exemplary implementation, depositing the Au/Ti bilayer on the substrate layer with the nano-roughened patterned region may further include electrically passivating an area of the Au/Ti bilayer except the array of microelectrodes and the array of electrical connections. In another exemplary implementation, depositing the Au/Ti bilayer on the substrate layer with the nano-roughened patterned region may further includes removing the Au/Ti bilayer except the array of microelectrodes and the array of electrical connections.

In an exemplary implementation, forcing the attachment between the at least one HUVEC and the at least one microelectrode on the biosensor may include applying an electrically active positioning system to adhere the at least one HUVEC on the at least one microelectrode utilizing a dielectrophoresis (DEP) technique.

In an exemplary implementation, stripping the photoresist layer from the substrate layer may include removing the photoresist layer from the substrate layer by solving the photoresist layer in a solvent.

In an exemplary implementation, the exemplary method may further include depositing an electrically insulator layer on surface of the biosensor except surface of the array of microelectrodes.

DETAILED DESCRIPTION

Figure 1A:
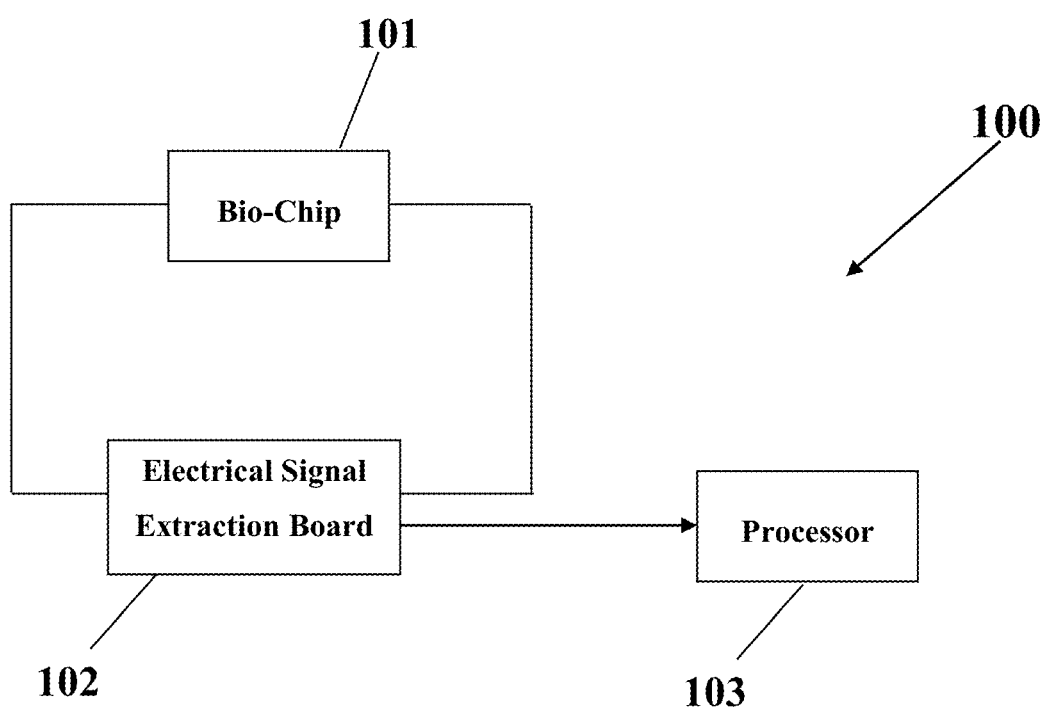
FIG. 1A illustrates a schematic of an electrical system for diagnosis of metastasis, consistent with one or more exemplary embodiments of the present disclosure.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Intravasation of metastatic cells into blood stream initiated by their invasion to endothelial barrier of vascular layer would be a significant diagnostic characteristic of metastasis. Many proteins implicated in tumor metastasis have been identified to act either as negative, such as E-Cadherin, or positive, such as $\alpha v \beta 3$, 4, 6, CD24, and CXCR2 factors. Expression of positive proteins started by disruption in basement membrane, adhesion of tumor cells to vascular endothelium, retraction of endothelial junctions or necrosis of some endothelial cells. In vitro models are utilized to investigate the invasive ability of unknown cells removed from the patients to vascular layer turned to an interested field in metastatic diagnosis. The simple setup, the easy readout, the kinetic analysis, the evaluation of cell morphology and the feasibility to perform the assay with standard laboratory equipment are some of the challenges limiting the usability of developed methods.

The strength of the cancer cells invasion to endothelial barrier may be a strong indication for metastatic ability of tumor cells. Investigating the possible expression of metastasis related proteins required, complicated biochemical processes, along with expensive biomarkers and skillful operators make it a difficult process especially when the number of metastatic cells are so rare. The various components of tumor-endothelial cells interactions can be simulated in vitro by challenging a monolayer of Human Umbilical Vein Endothelial Cells (HUVECs) with removed tumor cells from a patient. Investigations implicated by electron and phase-contrast imaging indicated that the in vitro sequence of events fairly represent the in vivo metastatic process. However, fabricating an integrated diagnostic system to evaluate metastatic ability of unknown tumors based on their invasion to endothelial barriers is still a challenge which limits the entrance of vascular invasion assay in clinics. Some electrical biosensors have been introduced based on changed electrical response of the HUVEC covered microelectrodes after their interaction with tumor cells. Some major limitations restricted their development, including: first, an adhesive layer such as fibronectin, laminin or collagen is required to enhance the attachment of HUVEC cells to the electrodes. Electrical capacitance made by such layers has been reported to be in similar ranges measured for HUVEC cells which would perturb the response of the sensor. Second, minimum concentration of cancer cells required to induce measurable changes in the electrical signals of the sensor (by retracting the HUVEC barrier) must be further than their real value in patients' tumor, for example, one cancer cells per 2.5 HUVEC cells. It wouldn't be applicable in clinical trials in which tracing the rare concentration of metastatic cells would be so crucial. Applying advantages of new technologies such as nanotechnology, photonics and tissue engineering may help to provide new assays with better efficiencies.

Herein, an impedimetric invasion assay is described to diagnose metastatic cells from primary cancerous ones, for example, in an unprocessed sample resected from a patient without any need for an adhesive layer or an excess amount of cancer cells within the sample. Using a low concentration of tumor cells in this invasion assay may open the way for its application in clinical experiments.

Disclosed herein is an exemplary system and an exemplary method to detect the presence of invasive/metastatic cells in a metastatic-suspicious sample, for example, an unprocessed tumor/lymph node sample of a cancer patient such as a breast cancer patient. Herein, an exemplary electrical impedimetric system and method with the assistance of a bio-chip is described to monitor the invasion of rare metastatic cells to endothelial barrier so that the metastatic cells may be diagnosed within an unprocessed sample via a label-free approach. The present disclosure includes an integrated optical-electrical system and method including both electrical and optical monitoring the invasion of metastatic cells to the HUVECs for metastasis prognosis or diagnosis at early stages for unprocessed resected samples.

The diagnostic principles of the exemplary embodiments consistent with present disclosure may be fundamentally different from that of marker-based pathological methods. Herein, the metastatic cells may be captured in a freshly removed solid or liquid sample in single or cluster forms due to their invasive activity regardless of their morphology and marker binding affinity. Thus, allowing detection of metastatic cells that might otherwise escape from labeling and staining. Moreover, captured cells may be retained under a live dynamic function, unlike with assays where cells are fixed, lysed or exposed to damaging stresses, for example, IHC, RT-PCR, etc. assays. So the captured metastatic cells could be reanalyzed by marker based methods, for example, epi-fluorescence microscopy. In addition, other types of the cells existed in the biopsied tissue like non-invasive epithelial cells, peripheral lipids and blood cells may not apply invasive interaction by HUVEC traps so wouldn't be captured by the disclosed system and method. As a result, no false alarms should be reported by the present disclosed system and method. This technology may enable scan-free processing of the whole-sample.

In the present disclosure, the term "sample" may refer to a metastatic-suspicious sample that may include a cell line or a biopsied small amount of a patient tissue that may be either solid or liquid and may be analyzed for cancer diagnosis.

FIG. 1 shows a schematic of an electrical system 100 for diagnosis of metastasis in a metastatic-suspicious sample, consistent with one or more exemplary embodiments of the present disclosure. The electrical system 100 may include an impedimetric system to measure and monitor the electrical impedance for metastasis diagnosis. The system 100 may include a bio-chip 101, an electrical signal extraction board 102, and a processor 103. The bio-chip 101, the electrical signal extraction board 102, and the processor 103 may be electrically connected to each other. The metastatic-suspicious sample may be introduced into the bio-chip 101 and the diagnosis of metastasis may be done via monitoring a set of time-lapse electrical signals that may be recorded by the processor.

In an exemplary embodiment, the electrical signal extraction board 102 may be configured to apply a voltage on an array of electrodes of the bio-chip 101 and receive the set of time-lapse electrical signals from the array of electrodes of the bio-chip 101. The received set of time-lapse electrical signals may be sent to the processor 103 that may be configured to record and analyze the electrical signals received by electrical signal extraction board 102 to detect a metastasis condition.

In an exemplary implementation, about 400 mV of voltage may be applied on the array of electrodes of the bio-chip 101. The applied voltage may have a frequency between about 1 KHz and about 150 KHz.

In an exemplary implementation, the set of time-lapse electrical signals may include a set of time-lapse electrical impedance values. Furthermore, a metastasis condition may be detected by the system 100 via monitoring and analyzing the time trend variations of the time-lapse electrical signals. A metastasis may be detected if the time-lapse electrical signals have a reducing trend with a reduction amount of more than about 50% reduction, or in some examples, more than about 70% reduction within a time interval of at least about 4 hours after loading the metastatic-suspicious sample into the biosensor 101. The metastatic-suspicious sample may be a cell line from a cell bank, for example, epithelial cell lines that may include MCF-7 cell lines. Moreover, the sample may be an unprocessed sample that may be resected from a cancer patient, for example, a breast cancer patient.

Figure 1B:
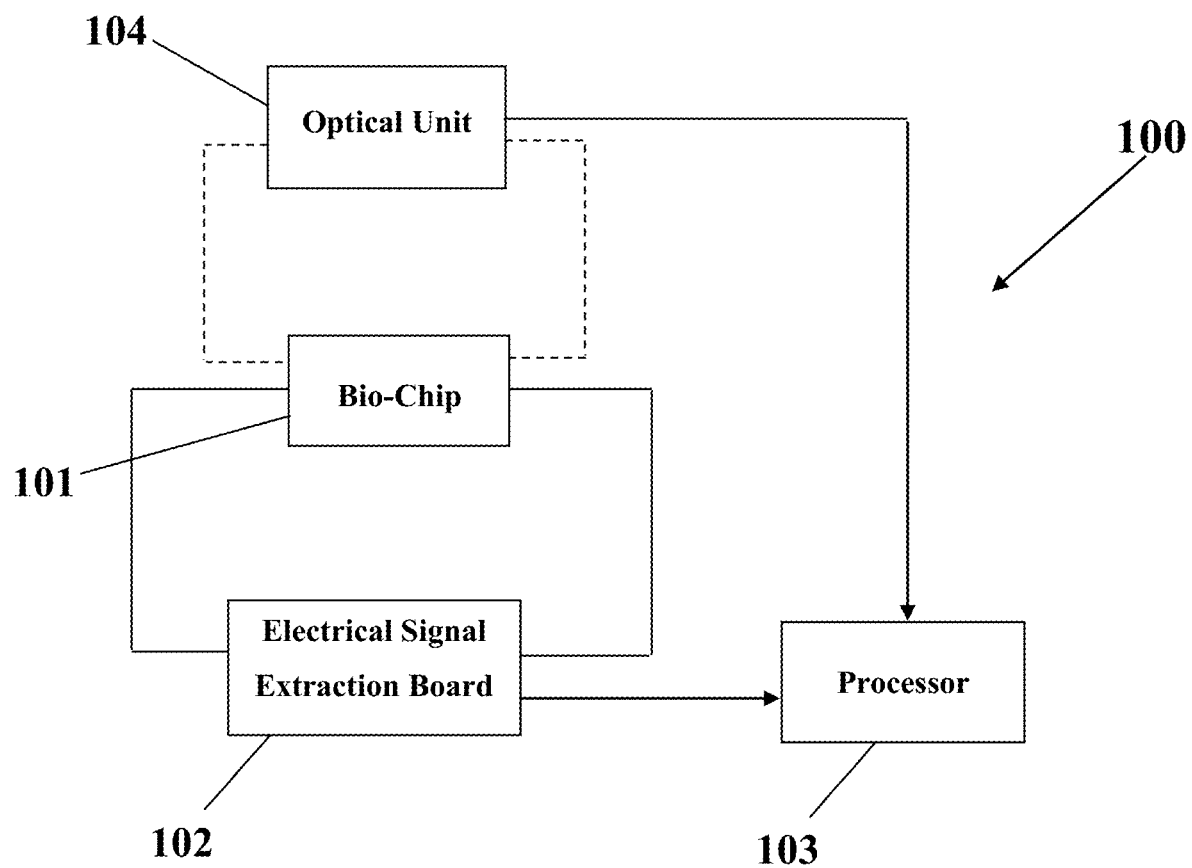
FIG. 1B illustrates a schematic of an integrated optical-electrical system for diagnosis of metastasis, consistent with one or more exemplary embodiments of the present disclosure.

As shown in FIG. 1B, the system 100 may further include an optical unit 104 that may be configured to capture a set of time-lapse optical images from the biosensor 101. The optical unit may be connected to the processor. The processor 103 may concurrently record and analyze the set of time-lapse electrical signals received by the electrical signal extraction board 102 and the set of optical images taken by the optical unit 104 to detect a metastasis condition. The metastasis diagnosis may be conducted based on monitoring the set of time-lapse electrical signals and the set of optical images that may be recorded by the processor 103.

In an exemplary implementation, the processor 103 may include an analyzer software that may match the set of time-lapse electrical signals from the array of electrodes with the set of time-lapse images to evaluate the syndicate between a sharp reduction of electrical signals and HUVECs retraction by invasive metastatic cells. For example, an invert microscopic imaging system with phase contrast and florescent equipment may be embedded at the bottom of the biosensor substrate to record any invasive interactions in real time.

In an exemplary implementation, the processor 103 may utilize a software that may record the set of time-lapse electrical signals received by the electrical signal extraction board 102 and the set of time-lapse images taken by the optical unit 104. If an electrical signal drops below a threshold (30% of the first electrical signal of the time-lapse electrical signal), the system may warn the user about a potential metastasis occurrence and may show the affected trap on a screen of the processor 103 for visual confirmation.

In an exemplary implementation, metastasis may be diagnosed or detected by the system 100 of FIG. 1B if the set of time-lapse electrical signals have a reducing trend with a reduction amount of for example, more than about 50% reduction, or in some examples, more than about 70% reduction and also an invasion of a metastatic cell to a HUVEC may be observed in an image of the set of optical images taken by the optical unit 104. The metastasis diagnosis may be done during a time interval of at least 4 hours after loading or introducing the metastatic-suspicious sample into the bio-chip 101.

Figure 2A:
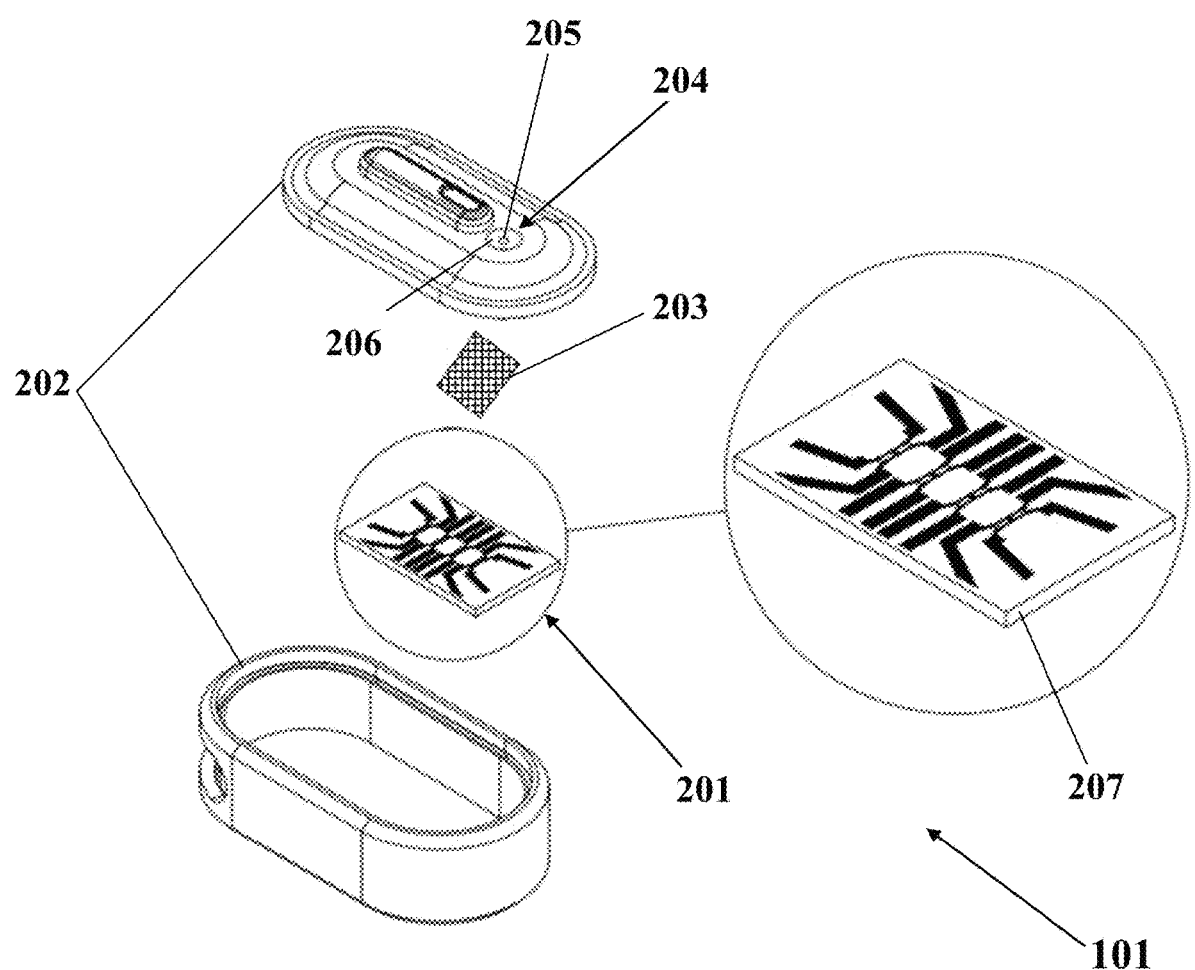
FIG. 2A illustrates a schematic of a bio-chip used for diagnosis of metastasis, consistent with one or more exemplary embodiments of the present disclosure.

FIG. 2A illustrates a schematic of a bio-chip 101 of the system 100 that may be used for diagnosis of metastasis, consistent with one or more exemplary embodiments of the present disclosure. The bio-chip 101 may include a biosensor 201, an outer body 202, and a filtering member 203.

In an implementation, the outer body 202 may be placed around the bio-chip for example, for protecting purposes and easily clinical utilizing of the biosensor 201. The outer body 202 may include a cavity 204 that may be embedded on top of the outer body 202 that may be configured for introducing or adding a sample that is suspicious to include a metastatic cell.

In an exemplary implementation, the cavity 204 may include a hole 205 and a reservoir 206 shown in FIG. 2A. The volume of the cavity may be about 200 μl. The cavity 204 may be embedded on top of the outer body 202 to introduce a biopsied sample funneling the detached cells through the single HUVECs sensing traps to mediate the invasion conditions.

In an exemplary implementation, the filtering member 203 may be placed between the hole 205 and the biosensor 201, and may be used for filtering a sample entered from the hole 205. The filtering member 203 may prevent entering of impurities, contaminations, or residuals along the entered sample. The filtering member 203 may include a grid with a mesh size in a range of about 25 µm to about 50 µm and the grid may be made of Gold.

Figure 2B:
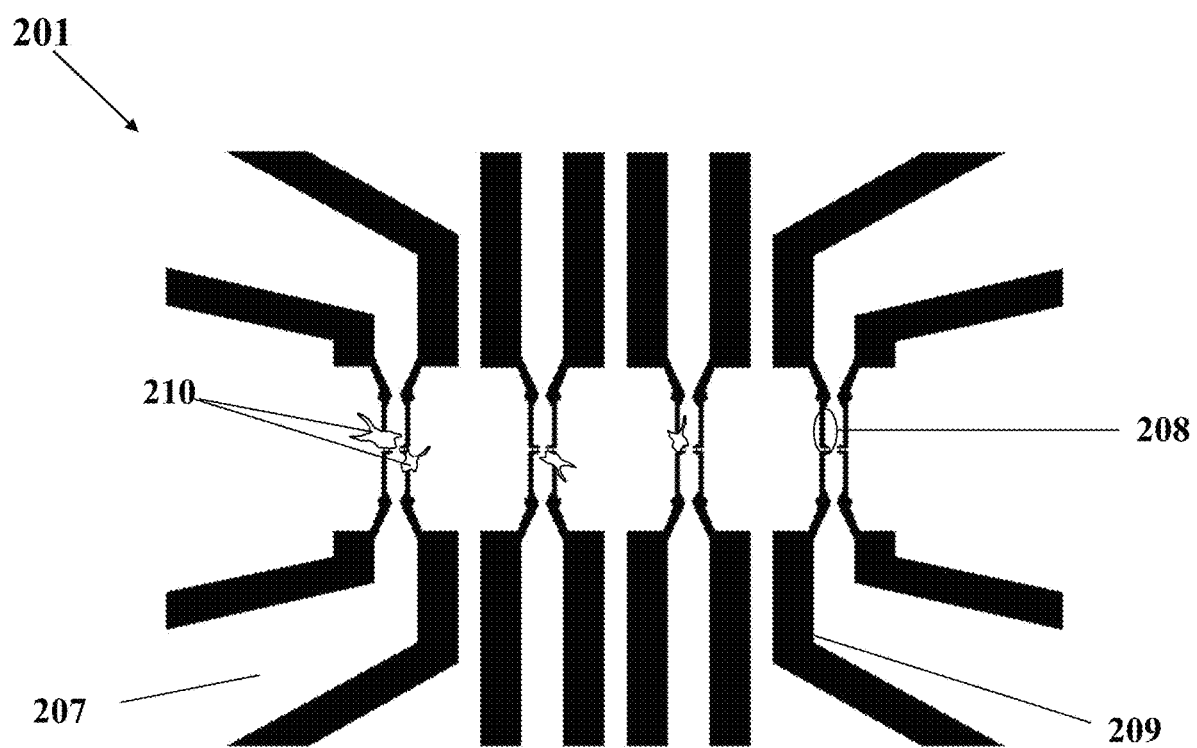
FIG. 2B illustrates a schematic of a biosensor for diagnosis of metastasis, consistent with one or more exemplary embodiments of the present disclosure.

FIG. 2B illustrates a schematic of a biosensor 201 for diagnosis of metastasis, consistent with one or more exemplary embodiments of the present disclosure. The biosensor 201 may include a substrate 207, an array of electrodes 208, and at least one Human Umbilical Vein Endothelial Cell (HUVEC) 210. The array of electrodes 208 may be electrically connected to the electrical signal extraction board 102 via an array of electrical connectors 209.

In an exemplary implementation, the substrate 207 may have a width of about 100 µm. The substrate 207 may include a silicon-based substrate or glass substrate, for example, the substrate may include a layer of Poly(methyl methacrylate) (PMMA) or a layer of Polydimethylsiloxane (PDMS). The PMMA, PDMS and other examples of a substrate 207 material, which may be used in exemplary embodiments may provide a biocompatible hydrophobic surface for use in the present cancer cells diagnosis applications.

In some exemplary embodiments, the substrate 207 may include a roughened surface, for example, a nano-roughened surface for enhanced adhesion of the HUVECs 210 on the substrate 207. The nano-roughened surface may be applied to enhance HUVECs 210 adhesion via increasing hydrophobicity and cell-substrate contact sites instead of applying an adhesive layer between the HUVECs 210 and the substrate 207. Also, the nanostructured surface may improve direct electrical contact between the HUVECs 210 and the surface of the substrate 207. A fast adhesion and slow proliferation of HUVEC cells on such surfaces may stop the overgrowing of the cultured HUVECs endothelial layer during testing of the invasion assay.

In an exemplary implementation, the array of electrodes 208 may be patterned on the substrate 207, for example, with a regular pattern or a non-regular pattern. In a specific example, the array of electrodes 208 may be patterned on the substrate 207 with a parallel regular pattern or a circular regular pattern. The array of electrodes 208 may include an array of microelectrodes that may be made of gold and with a size approximately equal to the size of HUVECs 210.

Referring to FIG. 2B, a plurality of HUVECs 210 may be attached or adhered on the substrate 207 to form a plurality of biological traps for a metastatic cell. In exemplary embodiments, at least one single HUVEC 210 may be attached on one electrode of the electrodes 208 placed on the substrate 207. In an exemplary embodiment, the single HUVEC 210 may be individually attached on the one electrode so that it covers a portion of the electrode and the substrate 207. The HUVEC 210 may prepare a biological trap for a metastatic cell that may tend to invade the HUVEC 210, consequently resulting in retraction of the HUVEC 210 from the electrode 208 so that a change in an electrical signal received from the electrodes 208 may occur.

Figure 3:
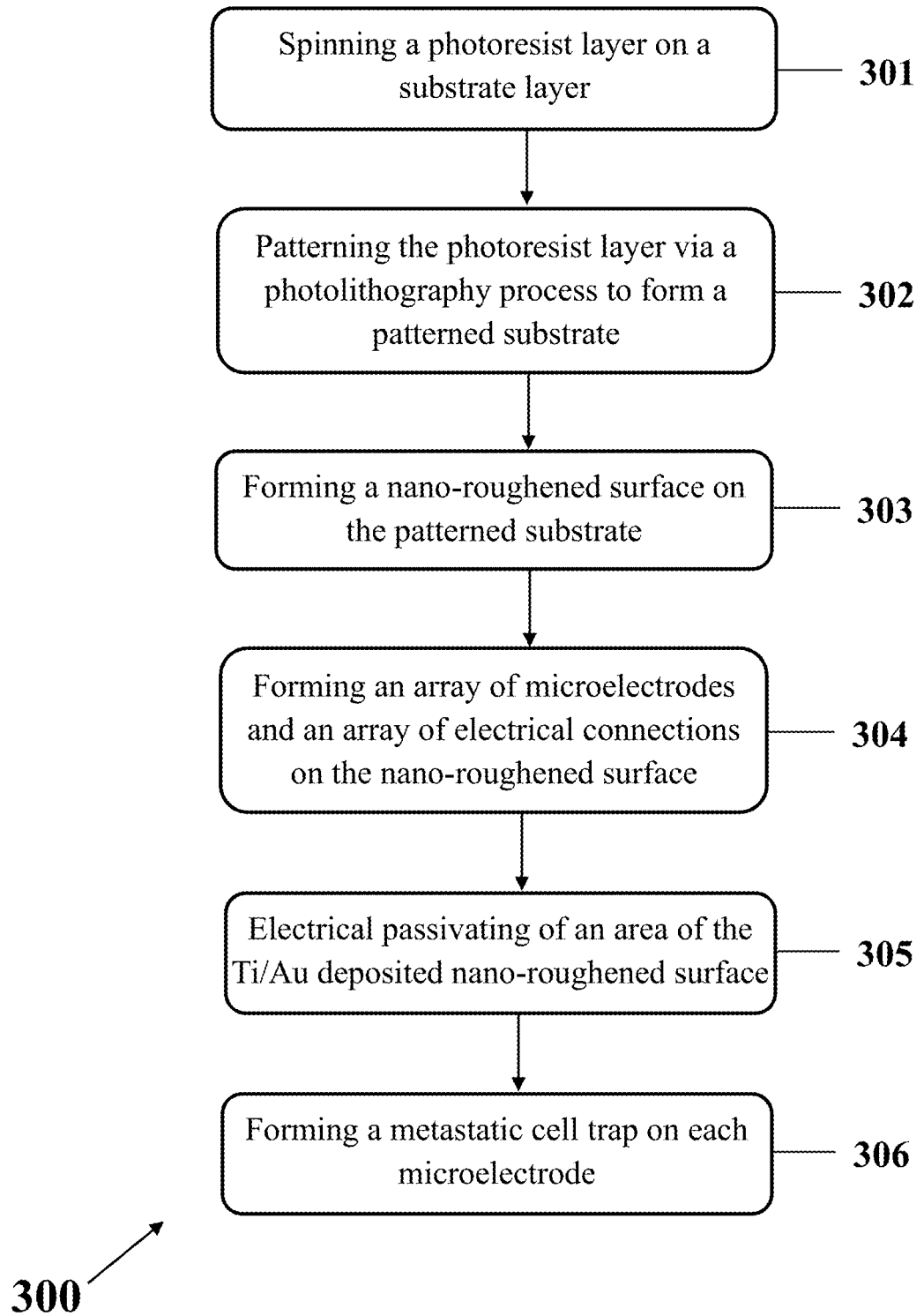
FIG. 3 illustrates a method to fabricate a biosensor with a nano-roughened surface for diagnosis of metastasis, consistent with one or more exemplary embodiments of the present disclosure.

In an exemplary embodiment, a method for fabricating a biosensor for metastasis diagnosis is disclosed, for example, biosensor 201 with a nano-roughened surface. FIG. 3 illustrates a method 300 to fabricate the biosensor 201 with a nano-roughened surface for diagnosis of metastasis. Referring to the method 300, it may include spinning a photoresist layer on a substrate layer (step 301), patterning the photoresist layer via a photolithography process to form a patterned substrate (step 302), forming a nano-roughened surface on the patterned substrate (step 303), forming an array of microelectrodes and an array of electrical connections on the nano-roughened surface by depositing a bilayer of Ti/Au on the nano-roughened surface (step 304), electrical passivating of an area of the Ti/Au deposited nano-roughened surface except the array of microelectrodes and the array of electrical connections (step 305); and forming a metastatic cell sensing trap on each microelectrode (step 306).

In step 301, a layer of photoresist may be spin coated on the substrate 207, for example, a PMMA substrate. The photoresist layer may serve as a mask for making a nano-roughened structure on the substrate 207.

In step 302, the photoresist layer formed in step 301 may be patterned, for example, using a photolithography process so that a patterned substrate may be formed. The formed pattern may be a desired region for producing nano-features to obtain a nano-roughened substrate.

In step 303, a nano-roughened surface may be formed on the patterned substrate of the step 302. For this purpose, the patterned substrate obtained from step 302 may be placed in a reactive ion etching (RIE) system to form nano-sized roughened surface in the region of the patterns of the substrate 207.

In step 304, an array of microelectrodes and an array of electrical connections may be formed on the nano-roughened surface by depositing a bilayer of Ti/Au on the nano-roughened surface. The bilayer of Ti/Au may include a thin layer of titanium (Ti) with a thickness of, for example about 5 nm covered with a thin layer of gold (Au) with a thickness of, for example about 30 nm. The bilayer of Ti/Au may be deposited on the nano-roughened surface using a sputtering process.

In step 305, an area of the Ti/Au deposited nano-roughened surface may be electrically passivated except the array of microelectrodes and the array of electrical connections. In this step, the Ti/Au bilayer may be removed from the substrate surface except electrodes and connection lines to form the microelectrodes 208 only on nano-roughened region.

In step 306, one or more metastatic cell sensing traps may be formed on each of the microelectrodes 208 by adhering one or more HUVEC 210 on the biosensor 201. The metastatic cell sensing traps may be formed via: adding a solution of HUVECs 210 on the biosensor 201; and forcing an attachment between a HUVEC 210 and a microelectrode 208 on the biosensor 210, for example, using a dielectrophoresis process (DEP).

Figure 4:
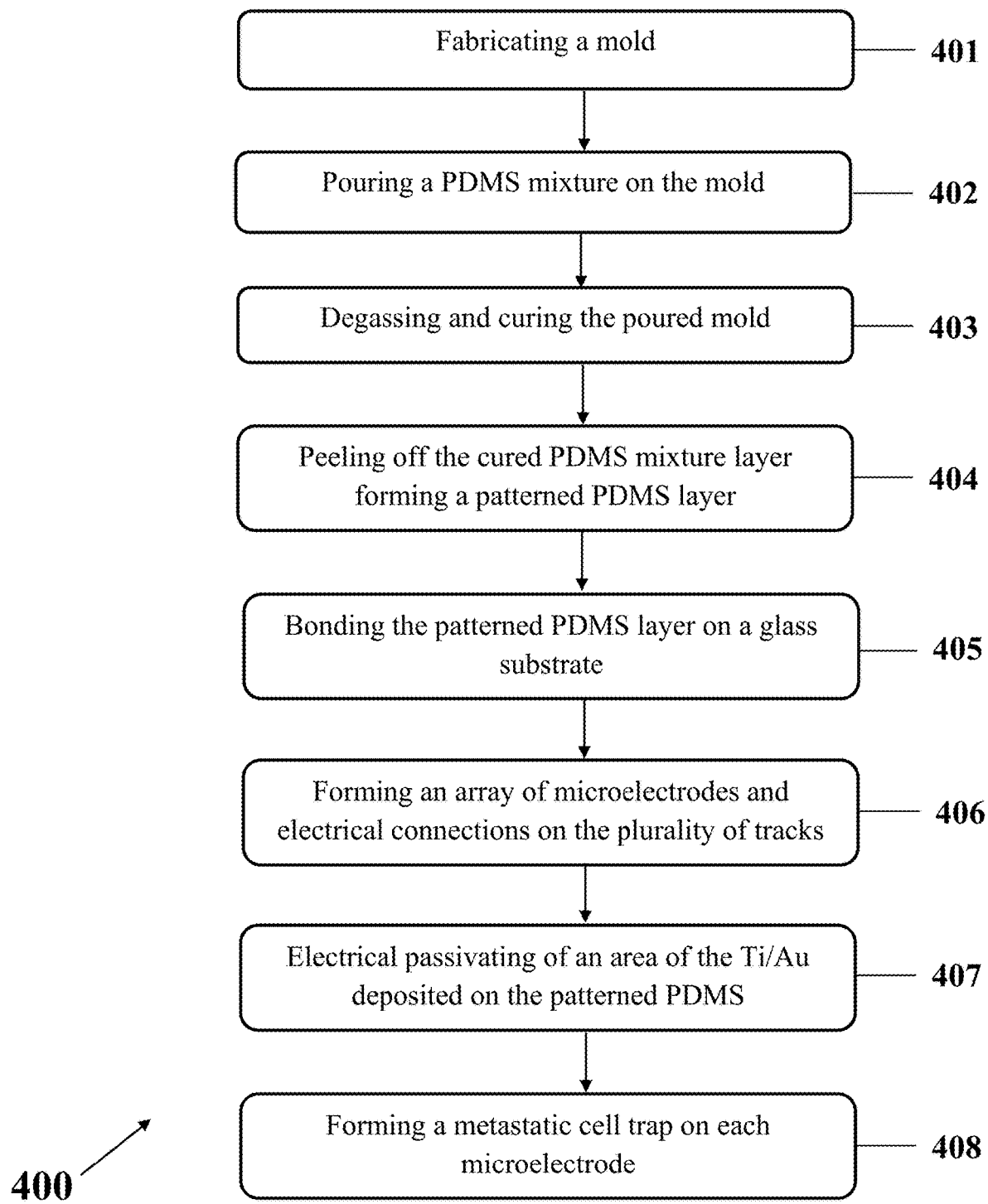
FIG. 4 illustrates a method to fabricate a biosensor with a PDMS substrate for diagnosis of metastasis, consistent with one or more exemplary embodiments of the present disclosure.
Figure 5A:
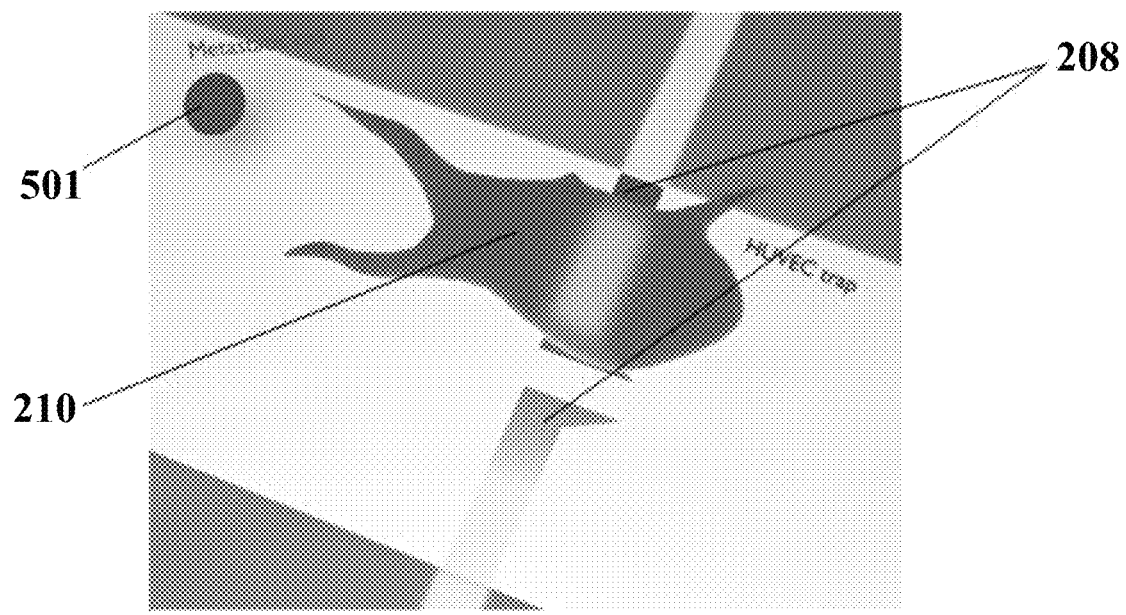
FIG. 5A-E illustrate a schematic of capturing and diagnosing a metastatic cell from unprocessed CNB sample derived from the lymph of any suspicious secondary tissue, based on the active interaction by a single vascular trap and retraction of the trap based on invasion of metastatic cell, consistent with one or more exemplary embodiments of the present disclosure.
Figure 5B:
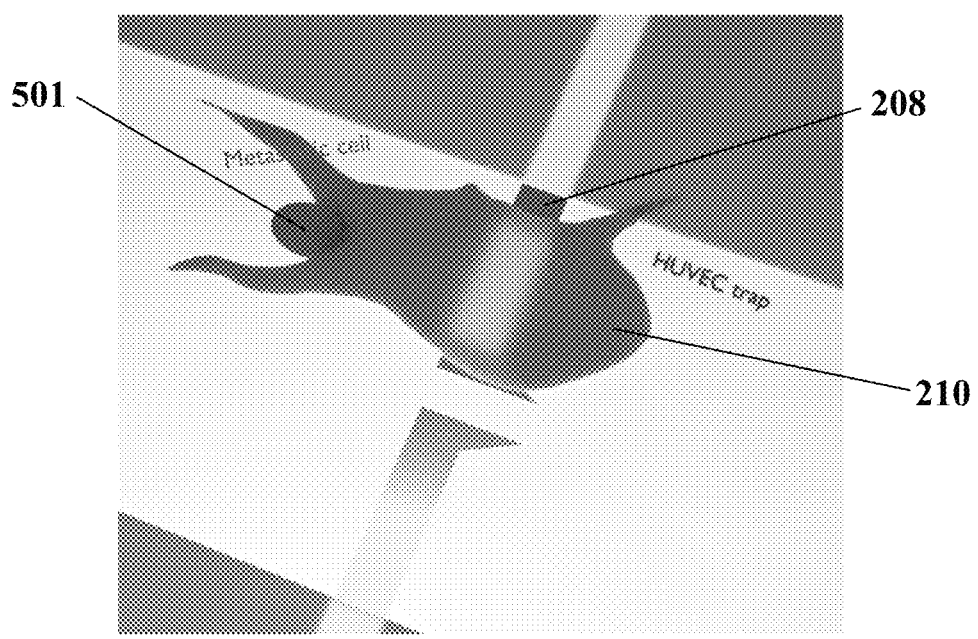
Figure 5C:
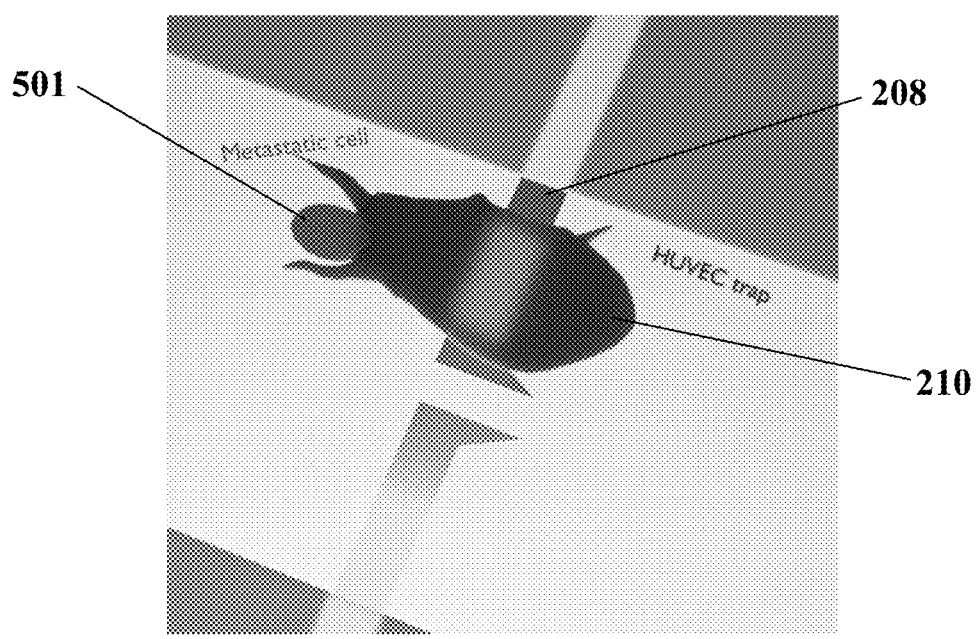
Figure 5D:
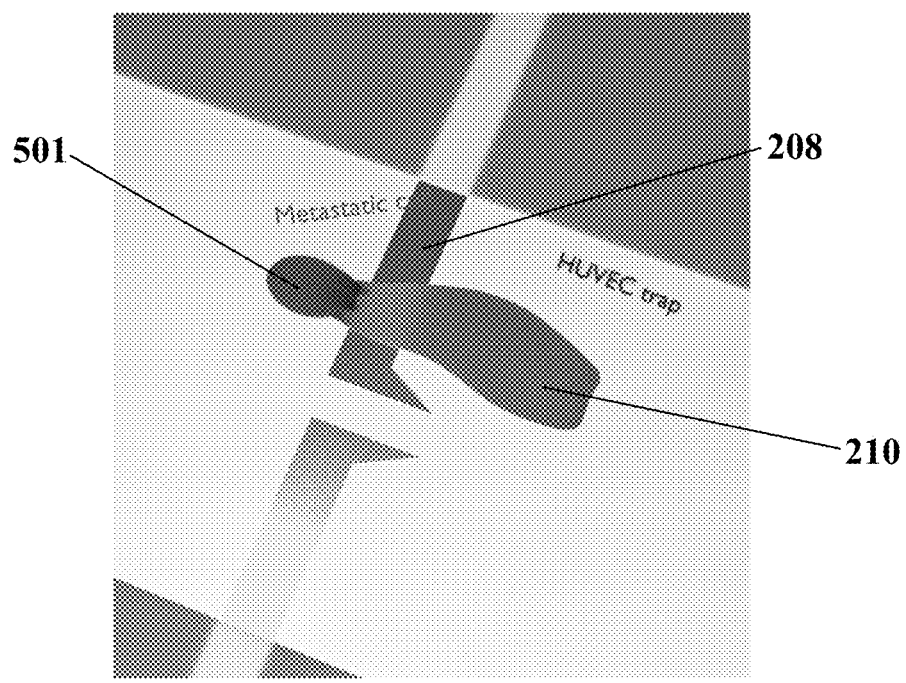
Figure 5E:
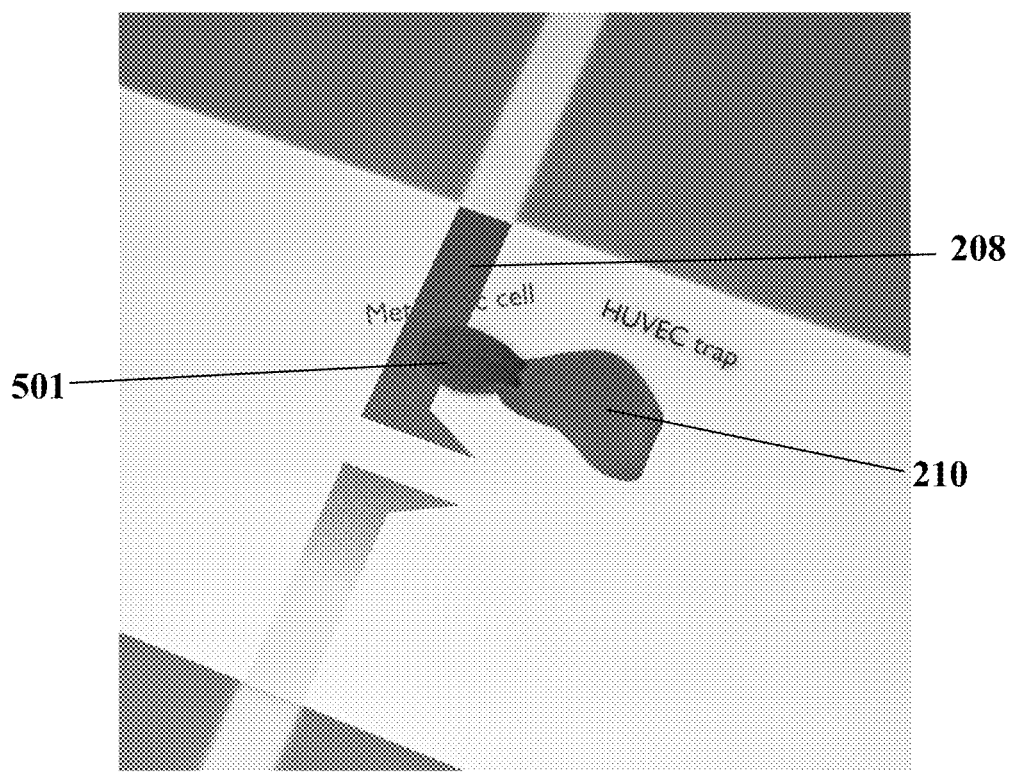

In another exemplary embodiment consistent with the present disclosure, a method for fabricating a biosensor for metastasis diagnosis, for example, the biosensor 201 is disclosed. FIG. 4 illustrates exemplary method 400 to fabricate the biosensor 201 with a nano-roughened surface for diagnosis of metastasis. Referring to this figure, the method 400 may include fabricating a mold (step 401), pouring a PDMS mixture on the mold (step 402), degassing and curing the poured mold (step 403), peeling off the cured PDMS mixture layer from the mold forming a patterned PDMS layer (step 404), bonding the patterned PDMS layer on a glass substrate (step 405), forming an array of microelectrodes and an array of electrical connections on the plurality of tracks via depositing a bilayer of Ti/Au on the patterned PDMS layer using a sputtering process (step 406), electrically passivating of an area of the Ti/Au deposited on the patterned PDMS except the plurality of tracks (step 407), and forming a metastatic cell trap on each microelectrode (step 408).

In step 401, a mold may be fabricated, for example, via a process that may include spinning a photoresist layer on a base layer, for example, a silicon wafer. Furthermore, it may entail patterning a plurality of microfluidic channels on the photoresist layer. For example, the plurality of microfluidic channels may be patterned on the photoresist layer using a photolithography process to obtain the mold.

In step 402, a mixture including the substrate 207 material may be poured on the mold obtained from step 401. The mixture may include a prepolymer, for example, PDMS and, a cross-linker.

In step 403, the poured mold obtained from step 402 may be degassed and cured. For example, the poured mold may be cured at a temperature of about 65° C. for at least about 4 hours after degassing.

In step 404, the cured PDMS mixture layer may be peeled off from the mold so that a patterned PDMS layer may be obtained. The obtained patterned PDMS layer may include a plurality of tracks that may later serve as a plurality of positions for the array of microelectrodes 208 and an array of electrical connections 209.

In step 405, the patterned PDMS layer may be bonded on a glass substrate. For example, the cured PDMS peeled off from the mold may be bonded with a glass substrate after a surface activation in oxygen plasma.

In step 406, an array of microelectrodes 208 and an array of electrical connections 209 may be formed on the plurality of tracks via depositing a bilayer of Ti/Au on the patterned PDMS layer bonded on the glass substrate in step 405. The Ti/Au bilayer may be deposited on the patterned PDMS layer, for example using a sputtering process.

In step 407, an area of the Ti/Au deposited on the patterned PDMS may be electrically passivated except the plurality of tracks, which may be the region of the array of microelectrodes 208 and the array of electrical connections 209. After the passivation, an ethanol solution may be flushed through the microfluidic channels and then the microfluidic channels may be washed, for example using deionized water and PBS before future uses for metastasis diagnosis.

In step 408, a metastatic cell trap may be formed on each microelectrode via a process that may include adding a solution of HUVECs on the biosensor 201 and forcing an attachment between a HUVEC 210 and a microelectrode 208 on the biosensor 201.

In an exemplary implementation, an electrically active positioning system may be applied as a preferred cell-registration technique to safely and rapidly place single HUVECs 210 on the microelectrodes 208. The HUVECs 210 may be individually adhered on the microelectrodes 208, for example by using a dielectrophoresis (DEP) technique applying a force on polarizable bodies in a non-uniform electric field. The registered single HUVEC cells 210 may play the role of active traps to capture the metastatic cells. The HUVECs 210 may maintain their positions after adhesion on the microelectrodes 208.

In an exemplary implementation, an array of single HUVECs 210 may be patterned and formed on the microelectrodes 208 within several minutes. A single HUVEC 210 may be spread to cover the surface of a registered electrode 208 in less than about 5 hours.

In an exemplary implementation, the disclosed system and method herein may diagnose a metastasis based on invasion tendency of the metastatic cells to the HUVECs. The exemplary system and method may be based on tracking the chemokines by metastatic cells, for example, chemokines S100A8 and S100A9 that may be released from HUVEC sensing traps. Metastatic cells may detach themselves from a biopsied sample or a cell line sample and retract the HUVECs traps. Retraction and detachment of HUVECs from the array of electrodes (microelectrodes), patterned on the biosensor surface, may induce sharp changes in electrical response, for example, an electrical impedance of the sensing elements that may match with some observable changes in optical images from the optical unit.

FIGS. 5A-E show an exemplary schematic of the invasion of an exemplary metastatic cell from an unprocessed CNB sample derived from the lymph of any suspicious secondary tissue, based on the active interaction of the metastatic cell 501 with a single vascular trap (HUVEC) 210. As it may be observed in FIGS. 5C-E, the invasion of the metastatic cell 501 may cause a retraction of the trap 210 from the microelectrode 208 resulting in reduces the electrical resistance of the sensing region, for example, a reduction in electrical impedance.

It should be understood that the presence of HUVEC sensing traps may stimulate the metastatic cells existing in a biopsied sample. The chemokines S100A8 and S100A9 that may be produced by endothelial vascular cells at the pre-metastatic niche may attract metastatic cells and facilitate their extravasation and invasion at the secondary site by inducing the formation of tumor cell invadopodia. Presence of MMP proteins at the external sites of invadopodia may be so crucial in their ability to proteolyse and disturb vascular cells. Hence, invasion to the vascular endothelial barrier may be one of the imminent steps of metastasis followed by entrance of cancer cells' nano-conduits into HUVECs and disturbing their morphology and proliferation. So the exemplary systems and methods may be optimized to handle the active migration of the detached metastatic cells without using any micro-pumps to induce flow speed.

In an exemplary implementation of the present disclosure, observing a sharp reduction, for example, about 80% in the time-lapse electrical responses diagrams, for example, in electrical impedance diagrams for at least one electrode covered by a HUVEC sensing trap, about 4 hours after introducing the biopsied sample or metastatic cell-lines to the biosensor may indicate an invasive interaction between a cell and a HUVEC trap. If this sample has been resected from the primary organ, the cancer may be invasive and if it has been removed from the peripheral tissues, for example, sentinel lymph nodes (in breast cancer), the cancer may have entered the micro-metastatic stage.

In an exemplary embodiment, a method for metastasis diagnosis is disclosed. The method may be an electrical impedimetric method or an integrated electrical impedimetric-optical method for diagnosis or prognosis of metastasis based on the metastatic cells invasion to the HUVECs.

Figure 6A:
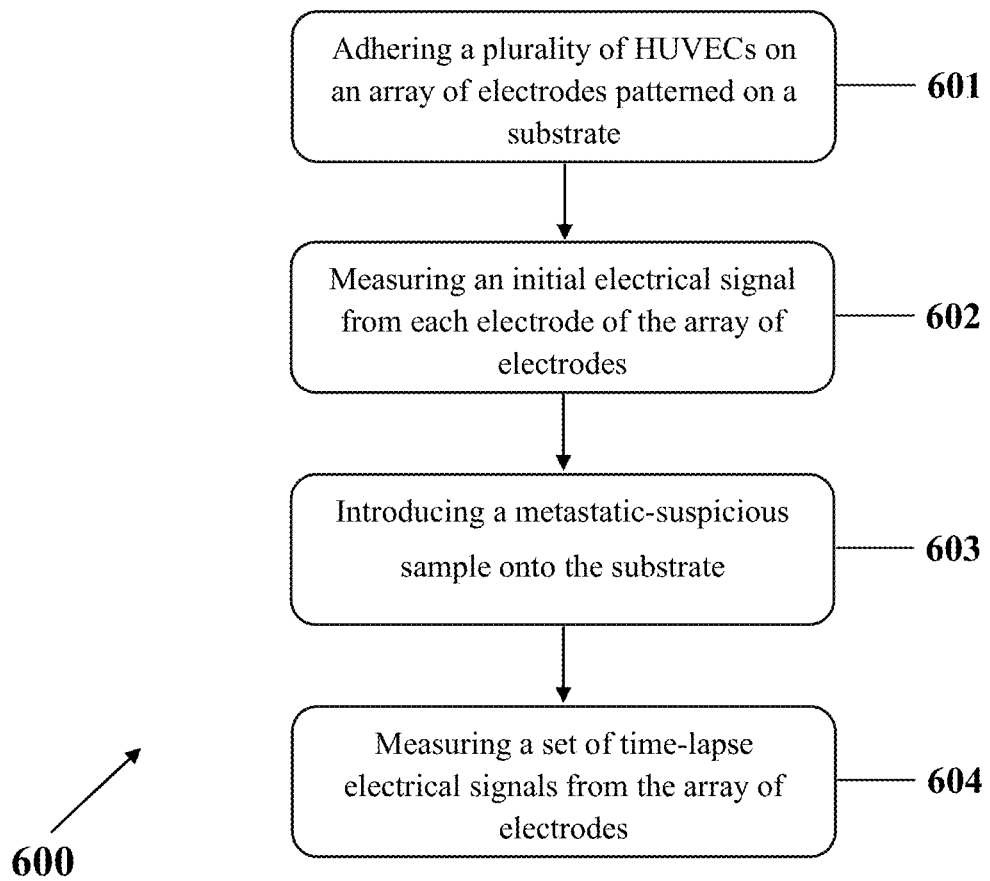
FIG. 6A illustrates a method for metastasis diagnosis, consistent with one or more exemplary embodiments of the present disclosure.

FIG. 6A shows an exemplary method 600 for metastasis diagnosis that may include adhering a plurality of Human Umbilical Vein Endothelial Cells (HUVECs) on an array of electrodes patterned on a substrate to cover the array of electrodes by HUVECs (step 601), measuring an initial electrical signal from each electrode of the array of electrodes (step 602), introducing a metastatic-suspicious sample onto the substrate (step 603), and measuring a set of time-lapse electrical signals from the array of electrodes (step 604). Each electrode may have an On/Off two-state that may include an On state for an entirely-covered electrode by a HUVEC and an Off state for a partially-covered electrode by a HUVEC. The metastasis diagnosis may include detecting a state change from On to Off for at least one electrode of the array of electrodes.

In step 601, an array of electrodes that may be patterned on a substrate, for example, a glass substrate, may be covered by a plurality of HUVECs. In an example, a single HUVEC may be selectively adhered on each electrode of the array of electrodes.

In an exemplary implementation, the adhering of the plurality of HUVECs on the array of electrodes may be conducted by applying an electrical field on the substrate that includes a solution including a plurality of HUVECs floated on the array of electrodes. In an example, adhering the plurality of HUVECs on an array of electrodes may be conducted by a method that may be one of an electrostatic cell patterning method, a dielectrophoresis (DEP) method, or a cell printing method.

In step 602, an initial electrical signal from each electrode of the array of electrodes may be measured. For example, the electrical signal may comprise an electrical impedance which is an electrical resistance of the electrode. In an On state for an electrode, the electrode may be entirely-covered by a HUVEC with a coverage of about 100%. In an example, each electrode may be entirely-covered by a HUVEC so that each electrode may have no initial electrical signal resulting an On state initially for the array of electrodes. In one exemplary implementation, the initial electrical signal may be measured using an electrical signal board and may be recorded by a processor for further analyses.

In step 603, a metastatic-suspicious sample may be exposed, entered, or introduced onto the substrate. The metastatic-suspicious sample may include an unprocessed living sample resected from a patient. The metastatic-suspicious sample may include a liquid or a solid metastatic-suspicious sample. The metastatic-suspicious sample may be resected by an operation that is selected from the group consisting of biopsy operation, core needle biopsy (CNB), endoscopy, colonoscopy, Lymph node aspiration and fine needle aspiration (FNA). In other examples, the metastatic-suspicious sample may include a plurality of cell lines.

In step 604, a set of time-lapse electrical signals may be measured from the array of electrodes. A metastatic sample may be diagnosed by monitoring a time trend of electrical signals including the initial electrical signal and the time-lapse electrical signals. Accordingly, if a state change from On to Off for at least one electrode of the array of electrodes is detected; then the metastatic-suspicious sample may be a metastatic sample and a metastasis may be diagnosed. The state change may occur within about 5 hours or less for a metastatic sample.

In an implementation, the set of time-lapse electrical signals includes a set of electrical impedances measured every 30 seconds after introducing the metastatic-suspicious sample onto the substrate. The set of time-lapse electrical signals may be measured for a time period of about 5 hours.

In an implementation, the state change from On to Off includes retraction of a HUVEC from an electrode, where the HUVEC was adhered on the electrode as a result of step 601. The retraction of the HUVEC from the electrode may result in a reduction in the measured electrical signals, for example, electrical impedance values. In an example, the state change from On to Off may include a 50% or more reduction of an electrical signal, for example, a reduction in electrical impedance within the set of electrical signals in comparison with the initial electrical signal for the electrode.

In an exemplary implementation, after complete spreading of each single HUVEC on the sensing traps, more than about 80% of the electrical current flowed through the electrode may be blocked. So a global response for all of the sensing traps in the biosensor related to the percent of blocked current may be defined. That may be equal to the increased impedance of the electrode. When a HUVEC completely covers whole of an electrode, the impedance blocking in about 4 kHz may be about 100% and the response of the sensing trap may be assumed as 1. In contrast, if the endothelial cell completely has been detached from its assigned single electrode, the impedance blocking would reach about 0% and hence the response may be assumed to 0. Any metastatic/invasive interaction with HUVEC sensing traps may retract the HUVECs from the electrodes and reduce the response of the electrode to about 0.

In an exemplary implementation, the method 600 may further include capturing a set of time-lapse optical images from the array of electrodes that may be captured concurrently with the step 604 to achieve a more accurate method for metastasis diagnosis.

In an implementation, the disclosed system and method may score as positive those samples that induces at least one reductive spike (1→0) in the electrical response diagram of at least one single HUVEC sensing trap, the metastatic interaction may be observed live in the set of time-laps images. Electrical responses and the optical images may validate diagnosis based on their individual traits, thereby, exhibiting great syndication.

Figure 6B:
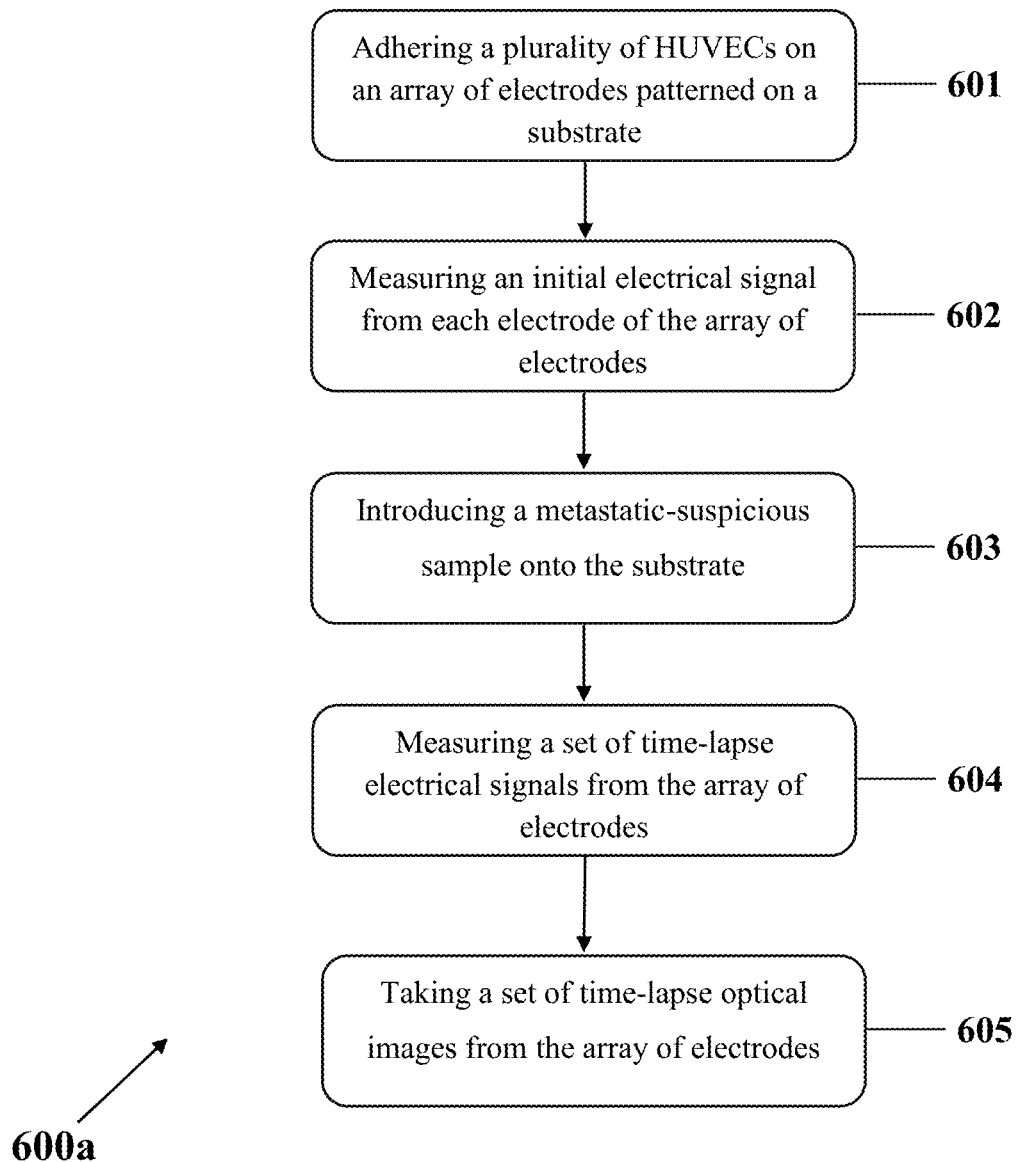
FIG. 6B illustrates an example integrated optical-electrical method for metastasis diagnosis, consistent with one or more exemplary embodiments of the present disclosure.

FIG. 6B shows method 600a for metastasis diagnosis that may include a further step 605 that may include taking a set of time-lapse optical images from the array of electrodes. In an example, the steps 604 and 605 may be synchronously performed with each other.

In step 605, a set of time-lapse optical images may be captured from the array of electrodes, for example, utilizing a microscope. The set of time-lapse optical images may include an initial image before introducing the metastatic-suspicious sample onto the substrate (step 603) and a plurality of time-lapse optical images after introducing the metastatic-suspicious sample onto the substrate (step 603).

Referring to method 600a, the metastasis diagnosis may include observing an invasion of a metastatic cell from the metastatic-suspicious sample to a HUVEC adhered onto an electrode in an optical image among the set of time-lapse optical images. In an example, the metastasis diagnosis may include detecting a state change from On to Off for at least one electrode of the array of electrodes and observing an invasion of a metastatic cell from the metastatic-suspicious sample to a HUVEC adhered onto an electrode in an optical image among the set of time-lapse optical images.

Figure 13A:
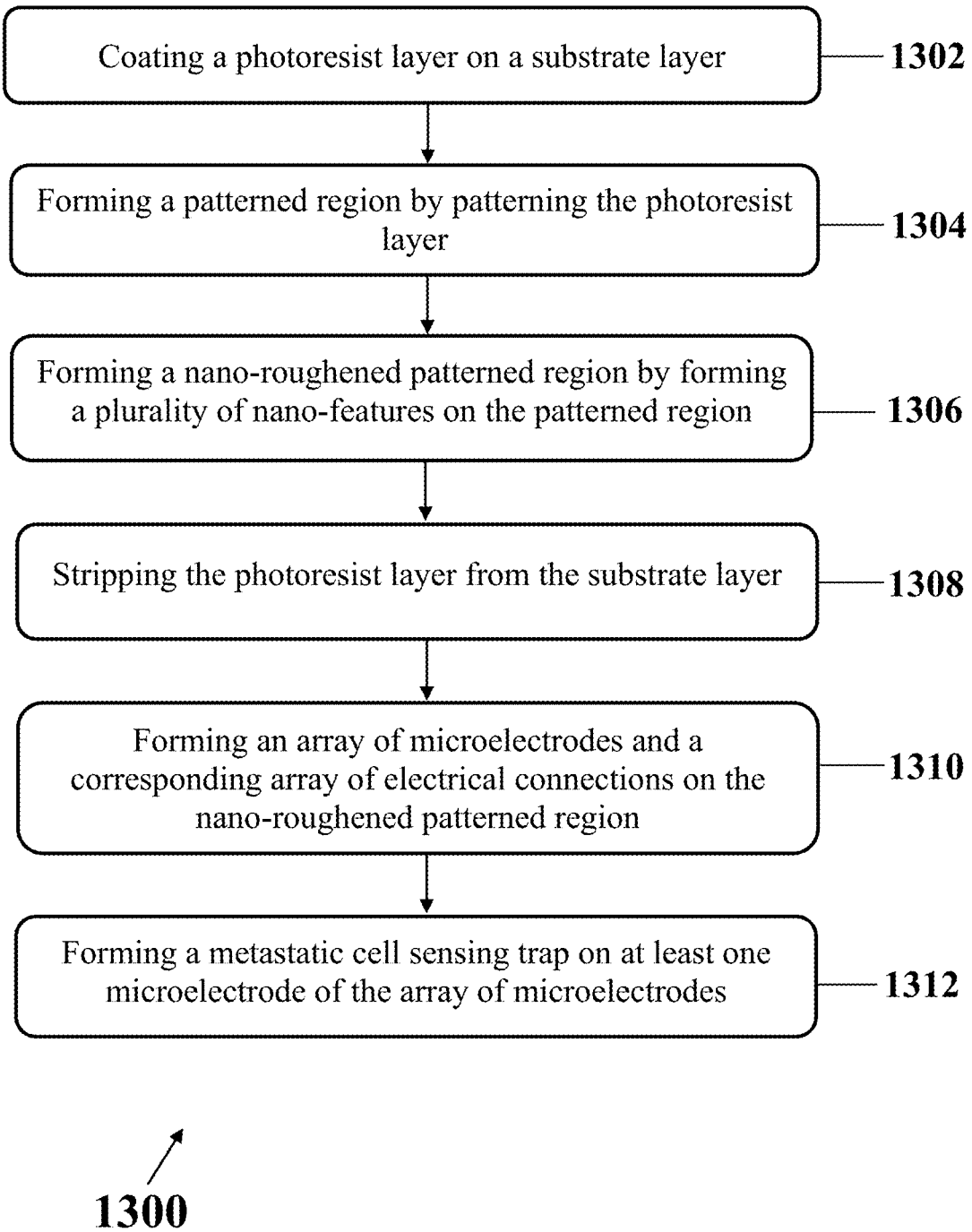
FIG. 13A shows an exemplary method for fabricating an exemplary biosensor for metastasis diagnosis, consistent with one or more exemplary embodiments of the present disclosure.

Exemplary methods and devices herein may have several implementations. In an exemplary implementation of the exemplary embodiments, exemplary biosensor 201 with various structures and arrangements of associated microelectrodes may be fabricated by various processes. FIG. 13A shows exemplary method 1300 for fabricating exemplary biosensor 201 for metastasis diagnosis, consistent with one or more exemplary embodiments of the present disclosure. Method 1300 may include coating a photoresist layer on a substrate layer (step 1302), forming a patterned region by patterning the photoresist layer (step 1304), forming a nano-roughened patterned region by forming a plurality of nano-features on the patterned region (step 1306), stripping the photoresist layer from the substrate layer (step 1308), forming an array of microelectrodes and an array of electrical connections on the nano-roughened patterned region (step 1310), and forming a metastatic cell sensing trap on at least one microelectrode of the array of microelectrodes (step 1312). Where, each electrical connection of the array of electrical connections may correspond to a respective microelectrode of the array of microelectrodes.

In detail, step 1302 may include coating a photoresist layer on a substrate layer. In an exemplary implementation, coating the photoresist layer on the substrate layer may include coating the photoresist layer on the at least one of a Poly(methyl methacrylate) (PMMA) layer and a glass layer. In an exemplary implementation, coating the photoresist layer on the substrate layer may include spinning the photoresist layer on the substrate layer. In an exemplary implementation, coating the photoresist layer on the substrate layer may include spin coating the photoresist layer on the substrate layer. In an exemplary embodiment, the photoresist layer may include an electrical insulator material. In some exemplary embodiments, the electrical insulator material may be a toxic material. In some exemplary embodiments, an electrical insulator material may be selected and utilized that may have a characteristic of losing its toxicity during a baking or a heating process.

Moreover, step 1304 may include forming a patterned region by patterning the photoresist layer on the substrate layer. In an exemplary implementation, forming the patterned region may include conducting a pre-treatment on the substrate layer or preparation of the substrate layer for forming an array of microelectrodes and a corresponding array of electrical connections with a designed (pre-determined) arrangement or a random arrangement on the substrate layer. In an exemplary implementation, forming the patterned region may include forming a pattern for decoration of the array of microelectrodes and the corresponding array of electrical connections on the photoresist layer. The pattern may include a pattern for an arrangement of the array of microelectrodes and the array of electrical connections respective to the array of microelectrodes on a surface of the substrate layer with the photoresist layer coated thereon. In an exemplary implementation, forming the patterned region may include forming the photoresist layer with a pattern thereon by forming a set of depressions and/or bulges on the photoresist layer. The set of depressions and/or bulges may form a set of locations for forming the array of microelectrodes and the corresponding array of electrical connections with the pre-determined pattern in step 1310. In an exemplary implementation, the formed patterned region of the photoresist layer may be firstly nano-roughened by forming a plurality of nano-sized hills in step 1306.

In an exemplary implementation, forming the patterned region may include patterning the photoresist layer on the substrate layer utilizing a photolithography process. In an exemplary implementation, forming the patterned region may include patterning the photoresist layer in form of a plurality of microchannels utilizing a photolithography technique using a chrome mask. The plurality of microchannels may be formed on the photoresist layer utilizing a photolithography process through a chrome mask and the formed plurality of microchannels may be the patterned region for depositing or forming the array of microelectrodes and the corresponding array of electrical connections thereon in following step 1310 of exemplary method 13.

In an exemplary implementation, forming the patterned region (step 1304) may include patterning the photoresist layer with a pattern, which may include one of a regular pattern for arrangement of the array of microelectrodes and a non-regular pattern for arrangement of the array of microelectrodes. Herein, the "pattern" refers to an arrangement design for the array of microelectrodes. Moreover, the "pattern" refers to an arrangement design for an array of electrical connections corresponding to the array of microelectrodes.

In an exemplary embodiment, the non-regular pattern may include a plurality of randomly patterned locations on the photoresist layer for the array of microelectrodes that may be formed by the photolithography technique. In an exemplary embodiment, the non-regular pattern may further include a plurality of randomly patterned locations on the photoresist layer for the array of electrical connections corresponding to the array of microelectrodes that may be formed by a photolithography technique. In an exemplary embodiment, the non-regular pattern may include a randomly formed patterned region with a non-specific layout or shape. In an exemplary embodiment, the randomly formed patterned region may include a plurality of randomly formed microchannels on the photoresist layer using the photolithography technique.

In an exemplary implementation, the regular pattern may include one of a parallel arrangement for the array of microelectrodes and a circular arrangement for the array of microelectrodes. In an exemplary implementation, forming the photoresist layer with the regular pattern may allow for forming a maximum number of microelectrodes and corresponding electrical connections on an available amount of surface of the substrate layer. In some implementations, the photoresist layer may be patterned with the circular arrangement in order to monitor all of the microelectrodes utilizing exemplary optical unit 104, for example, by a microscope at the same time.

Figure 14:
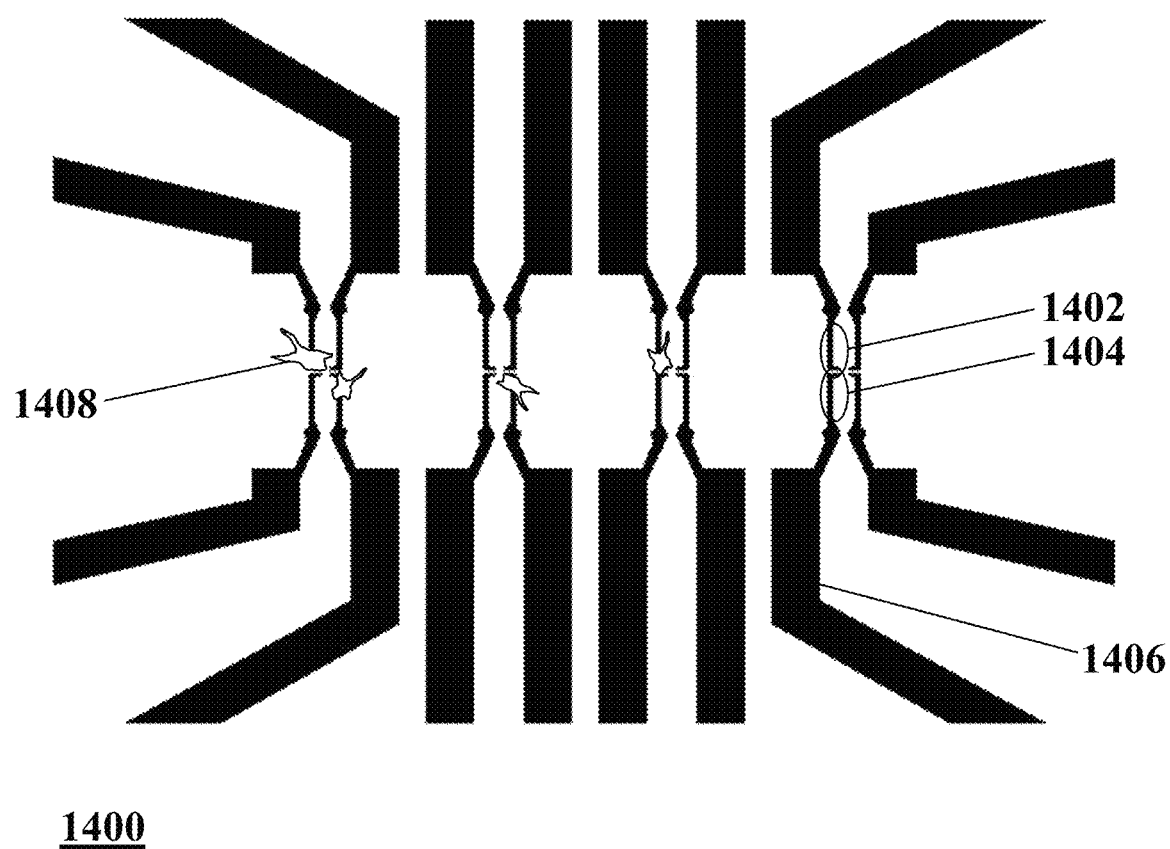
FIG. 14 shows a schematic view of surface of an exemplary biosensor with an exemplary parallel arrangement for the array of microelectrodes, consistent with one or more exemplary embodiments of the present disclosure.

FIG. 14 shows a schematic view of surface 1400 of exemplary biosensor 201 with an exemplary parallel arrangement for the array of microelectrodes, consistent with one or more exemplary embodiments of the present disclosure. In an exemplary embodiment, the parallel arrangement for the array of microelectrodes may include a plurality of couple electrodes, which may be placed parallel to each other. In an exemplary embodiment, each exemplary couple electrodes may include a first electrode 1402 and a second electrode 1404. In an exemplary embodiment, second electrode 1404 may be located at the bottom of the first electrode 1402. In an exemplary embodiment, a distance between the first electrode 1402 and the second electrode 1404 may be less than about 10 μm.

In an exemplary embodiment, the pattern of surface 1400 may further include an arrangement for the array of electrical connections corresponding to the array of microelectrodes. For example, each electrode 1404 of the array of microelectrodes may be connected to exemplary electrical signal extraction board 102 via a respective electrical connection 1406.

Figure 15:
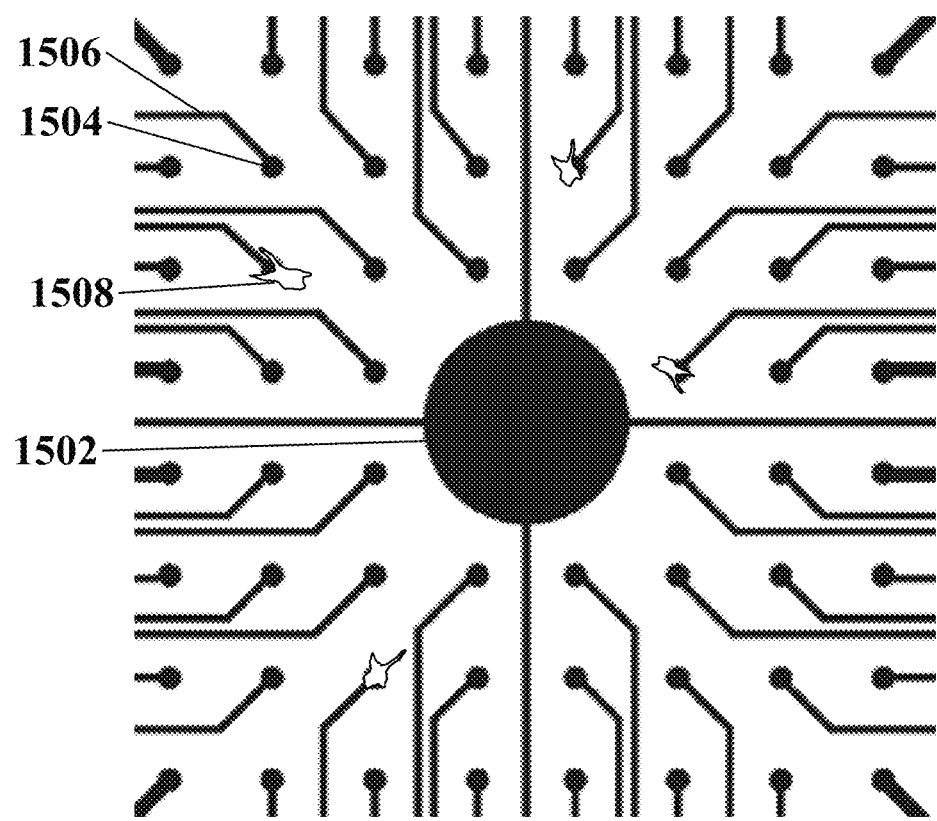
FIG. 15 shows a schematic view of surface of an exemplary biosensor with an exemplary circular arrangement for the array of microelectrodes, consistent with one or more exemplary embodiments of the present disclosure.

FIG. 15 shows a schematic view of surface 1500 of exemplary biosensor 201 with an exemplary circular arrangement for the array of microelectrodes, consistent with one or more exemplary embodiments of the present disclosure. In an exemplary embodiment, the circular arrangement for the array of microelectrodes may include exemplary electrical ground 1502 and a plurality of circular electrodes 1504 located around electrical ground 1502. In an exemplary embodiment, electrical ground 1502 may include a circular electrode at a center of the patterned region.

In an exemplary embodiment, the pattern of surface 1500 may further include an arrangement for the array of electrical connections corresponding to the array of microelectrodes. For example, each electrode 1504 of the array of microelectrodes may be connected to exemplary electrical signal extraction board 102 via a respective electrical connection 1506.

Figure 16:
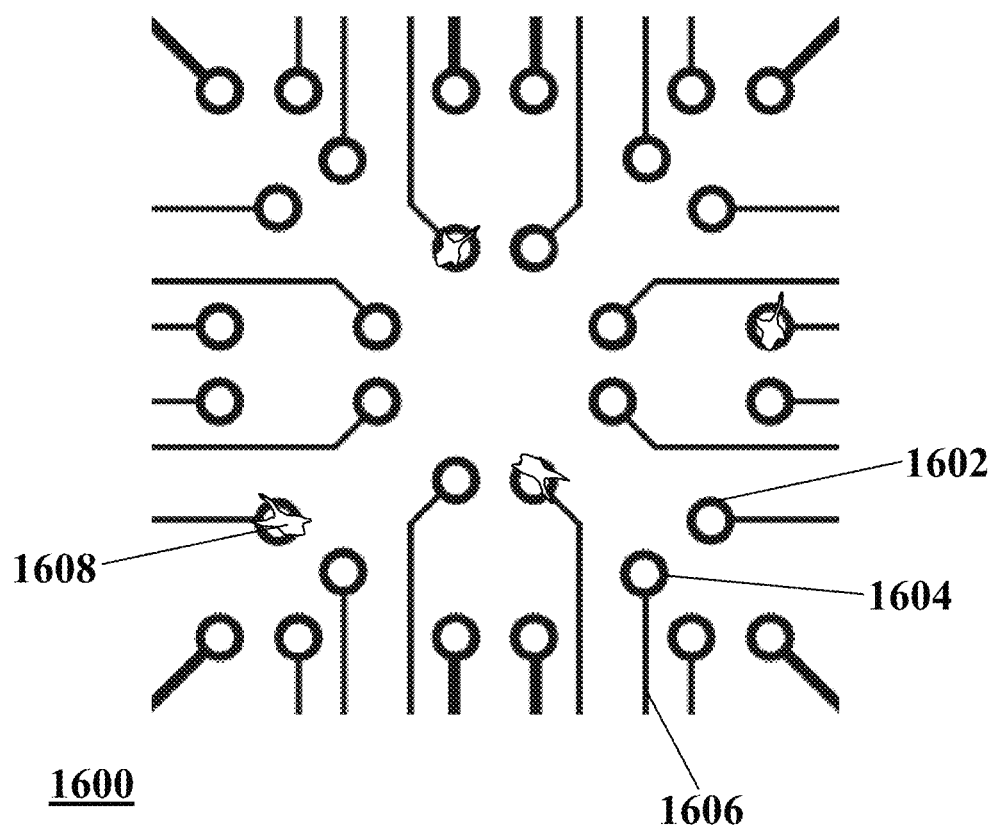
FIG. 16 shows a schematic view of surface of an exemplary biosensor with another exemplary circular arrangement for the array of microelectrodes, consistent with one or more exemplary embodiments of the present disclosure.

FIG. 16 shows a schematic view of surface 1600 of exemplary biosensor 201 with another exemplary circular arrangement for the array of microelectrodes, consistent with one or more exemplary embodiments of the present disclosure. In an exemplary embodiment, the circular arrangement for the array of microelectrodes may include a plurality of couple circular electrodes with a circular arrangement. In an exemplary embodiment, each exemplary couple electrodes may include a first circular electrode 1602 and a second circular electrode 1604, which may be located adjacent to the first electrode 1602. In an exemplary embodiment, a distance between the first electrode 1602 and the second electrode 1604 may be less than about 10 μm.

In an exemplary embodiment, the pattern of surface 1600 may further include an arrangement for the array of electrical connections corresponding to the array of microelectrodes. For example, each electrode 1604 of the array of microelectrodes may be connected to exemplary electrical signal extraction board 102 via a respective electrical connection 1606.

Referring again to FIG. 13A, step 1306 may include forming a nano-roughened patterned region by forming a plurality of nano-features on the patterned region. In an exemplary implementation, forming the nano-roughened patterned region may include nano-roughening a surface of the patterned region by forming the plurality of nano-features on the patterned region. In an exemplary implementation, forming the plurality of nano-features on the patterned region (step 1306) may include forming a plurality of nano-sized hills on the patterned region with a width of less than about 80 nm and a depth of less than about 120 nm for each respective hill of the plurality of nano-sized hills. In an exemplary implementation, forming the plurality of nano-features on the patterned region (step 1306) may include placing the substrate with the patterned region in a reactive ion etching (RIE) system and processing the patterned region by $SF_6$, $H_2$ and $O_2$ gases in the presence of RF Plasma.

Furthermore, step 1308 may include stripping the photoresist layer from the substrate layer. In an exemplary implementation, stripping the photoresist layer from the substrate layer (step 1308) may include removing the photoresist layer from the substrate layer by dissolving the photoresist layer in a solvent. In an exemplary implementation, stripping the photoresist layer from the substrate layer (step 1308) may include rinsing surface of the substrate with a solvent for the photoresist layer; allowing for dissolving the photoresist layer in the solvent and removing the photoresist layer from the substrate layer. In an exemplary implementation, stripping the photoresist layer from the substrate layer (step 1308) may include rinsing the photoresist layer with acetone.

In an exemplary implementation, step 1310 may include forming an array of microelectrodes and an array of electrical connections on the nano-roughed patterned region, where each electrical connection of the array of electrical connections may correspond to a respective microelectrode of the array of microelectrodes. In an exemplary embodiment, each electrical connection of the array of electrical connections may be corresponding to a respective microelectrode of the array of microelectrodes. In an exemplary implementation, the array of microelectrodes and the corresponding array of electrical connections may be formed on the nano-roughened patterned region by depositing a gold/titanium (Au/Ti) bilayer on the substrate layer with the nano-roughened patterned region; thereby, forming the array of microelectrodes and the corresponding array of electrical connections, that be made of gold, on the nano-roughened patterned region.

In an exemplary implementation, depositing the bilayer of Au/Ti on the substrate layer with the plurality of nano-features on the patterned region may be carried out utilizing a sputtering process. In an exemplary implementation, depositing the Au/Ti bilayer on the substrate layer with the nano-roughened patterned region may include depositing a Ti layer with a thickness between about 3 nm and about 10 nm on the substrate layer with the nano-roughened patterned region utilizing a sputtering process and depositing an Au layer with a thickness between about 10 nm and about 50 nm on the deposited Ti layer utilizing a sputtering process.

In an exemplary implementation, for precise electrical measurements, the only region that after forming the array of microelectrodes and the corresponding array of electrical connections continues to have an electrically conductive surface on surface of exemplary biosensor 201 may include the deposited Au/Ti bilayer on the array of microelectrodes and the corresponding array of electrical connections. Accordingly, in an exemplary implementation, depositing the Au/Ti bilayer on the substrate layer with the nano-roughened patterned region may further include electrically passivating an area of the Au/Ti bilayer except the array of microelectrodes and the corresponding array of electrical connections. In another exemplary implementation, depositing the Au/Ti bilayer on the substrate layer with the nano-roughened patterned region may further include removing the Au/Ti bilayer except the array of microelectrodes and the corresponding array of electrical connections.

In another exemplary implementation, for precise electrical measurements, the only region that after forming the array of microelectrodes and the corresponding array of electrical connections continues to have the electrically conductive surface on surface of exemplary biosensor 201 may include the deposited Au/Ti bilayer on the array of microelectrodes. Accordingly, exemplary method 1300 may further include depositing an electrically insulator layer on surface of exemplary biosensor 201 except surface of the array of microelectrodes.

Furthermore, step 1312 may include forming a metastatic cell sensing trap on at least one microelectrode of the array of microelectrodes. In an exemplary implementation, forming the metastatic cell sensing trap on at least one microelectrode of the array of microelectrodes (step 1312) may include adhering at least one Human Umbilical Vein Endothelial Cell (HUVEC) on at least one microelectrode of the array of the microelectrodes. In an exemplary implementation, forming the metastatic cell sensing trap on at least one microelectrode of the array of microelectrodes (step 1312) may include forming a metastatic cell sensing trap on each microelectrode of the array of microelectrodes. In an exemplary implementation, forming the metastatic cell sensing trap on at least microelectrode of the array of microelectrodes (step 1312) may include adhering an individual HUVEC on each microelectrode of the array of the microelectrodes; thereby, forming an array of individually adhered HUVECs onto the corresponding array of microelectrodes. In an exemplary embodiment, the sensing trap may be configured to trap a metastatic cell on the at least one microelectrode during invasion of the metastatic cell to the HUVEC.

Figure 13B:
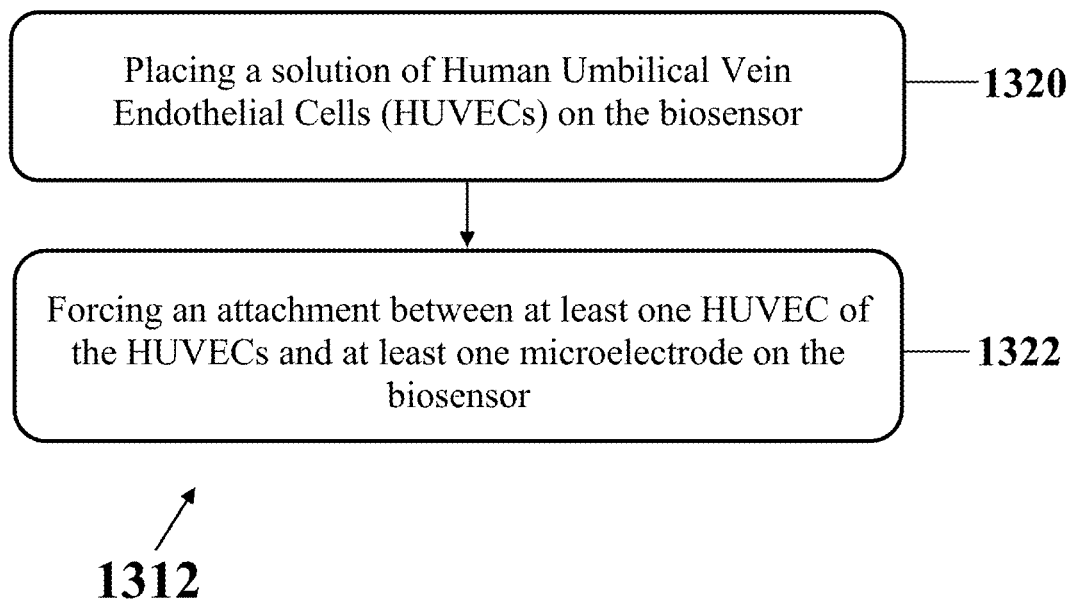
FIG. 13B shows an exemplary process for forming an exemplary metastatic cell sensing trap on each microelectrode of an exemplary array of microelectrodes, consistent with one or more exemplary embodiments of the present disclosure.

FIG. 13B shows an exemplary process for forming the metastatic cell sensing trap on the at least one microelectrode of the array of microelectrodes (step 1312), consistent with one or more exemplary embodiments of the present disclosure. Forming the metastatic cell sensing trap on the at least one microelectrode of the array of microelectrodes (step 1312) may include placing a solution of Human Umbilical Vein Endothelial Cells (HUVECs) on exemplary biosensor 201 (step 1320) and forcing an attachment between at least one HUVEC of the HUVECs and at the least one microelectrode on exemplary biosensor 201 (step 1322).

In an exemplary implementation, forcing the attachment between the at least one HUVEC and the at least one microelectrode on the biosensor may include applying an electrically active positioning system to the solution of HUVECs on exemplary biosensor 201 to adhere the at least one HUVEC on the at least one microelectrode utilizing a dielectrophoresis (DEP) technique. Referring to FIGS. 14, 15, and 16, the at least one HUVEC 1408, 1508, and 1608 may be respectively adhered on at least one microelectrode of the array of microelectrodes.

EXAMPLES

Example 1: Fabricating a Biosensor with a Nano-Roughened PMMA Substrate

In this example, a PMMA chip with a diameter of about 3 cm that may include an array of 6 circular shape microelectrodes with a diameter of about 200 μm was fabricated according to a simple and cheap process flow as may be described hereinbelow.

First, a thin layer of photoresist (Microposit 1813) was spin coated on the PMMA substrate as a mask for making nano-roughened structures. The photoresist layer was then patterned by a photolithographic process to obtain a desired region for producing nano-features. Subsequently, the substrate with a patterned photoresist layer was placed in a reactive ion etching (RIE) system. Thereafter, the patterned area was processed by $SF_6$, $H_2$ and $O_2$ gases (with typical flows of about 100 Sccm, about 80 Sccm and about 85 Sccm) in the presence of RF Plasma (at about 13.56 MHz) to form a nano-roughened surface. $SF_6$, which may be ionized in the presence of RF Plasma, may play the key role as the etching radical. The plasma power of the bombarding sub-cycle was about 150 W and the period of the bombarding sub-cycle was about 50 sec. A combination of $H_2/O_2$ and $SF_6$ during the settling step may result in the creation of a protecting layer over the side walls of the formed nano-hills in each sub-cycle. Using this method, a nano-roughened array were obtained on PMMA, with sizes down to about 60 nm in width and about 110 nm in depth. The resist layer was then stripped by acetone. Therefore, an Au/Ti bilayer (with a thickness of about 30/5 nm), was deposited on the PMMA using a sputtering process. The sputtering process was carried on by patterning the photoresist using reverse of the same mask containing the electrode design. Then, the Au/Ti bilayer was removed from the surface except electrodes and connection lines. So the metallic microelectrodes were formed exactly on the nano-roughened region. The prepared device was then bonded to a readout PCB and held in a cavity for biological tests.

Figure 7A:
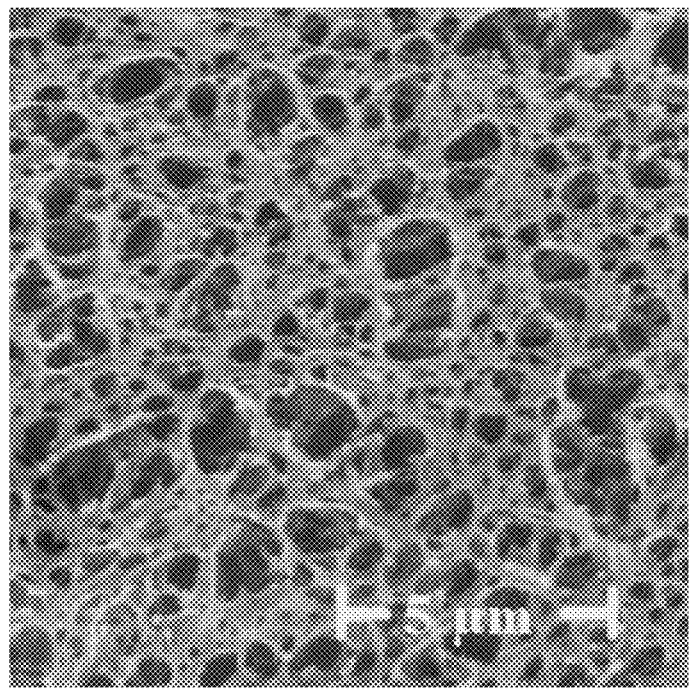
FIG. 7A illustrates a field emission scanning electron microscope (FESEM) micrograph of an example of a nano-roughened PMMA substrate, consistent with one or more exemplary embodiments of the present disclosure.
Figure 7B:
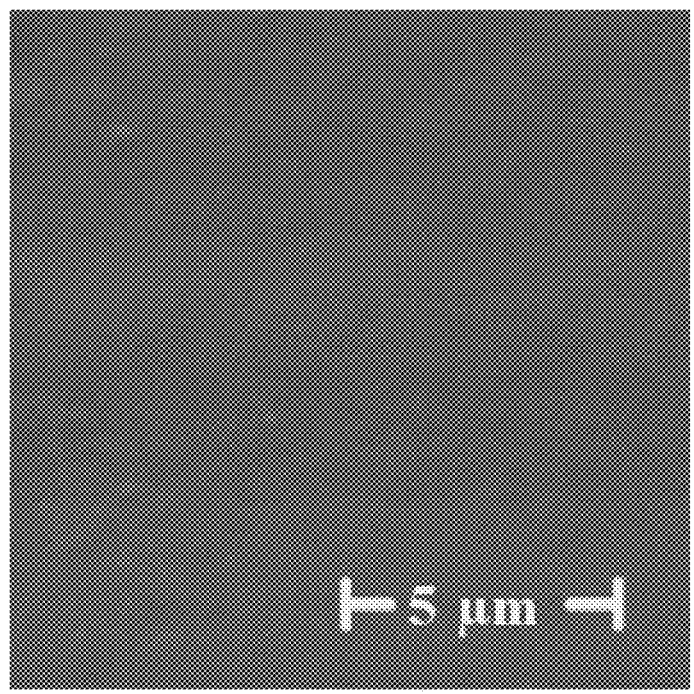
FIG. 7B illustrates a field emission scanning electron microscope (FESEM) micrograph of an example of a smooth PMMA substrate, consistent with one or more exemplary embodiments of the present disclosure.

FIGS. 7A and 7B show field emission scanning electron microscope (FESEM) micrographs of the surface morphology of a nano-roughened PMMA surface (FIG. 7A) and a smooth PMMA surface (FIG. 7B). Producing the nanostructures noticeably increased the roughness of the surface. It may be observed that the interactive surface of nano-indented surface (FIG. 7A) increased observably in comparison with a smooth PMMA substrate (FIG. 7B).

Human Umbilical Vein Endothelial Cells (HUVECs) were cultured in an EC basal medium (EBM) with additional about 10% FBS, and guaranteed to sub-cultured for three population doublings. To start cellular experiments, HUVEC cells were cultured on the surface of the biosensor for about 13 hours to form a confluent layer.

Figure 7C:
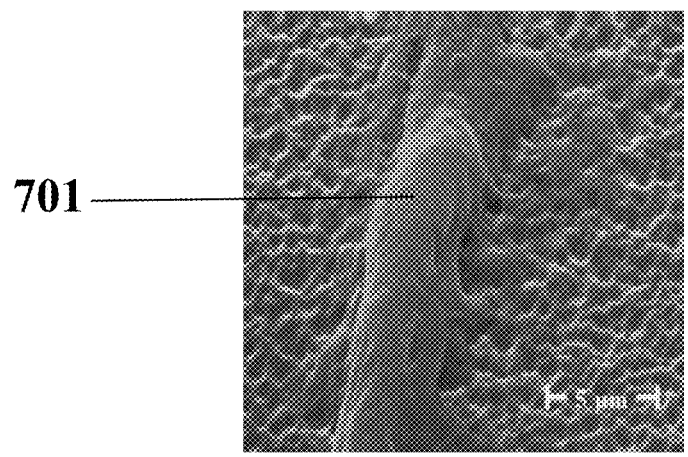
FIG. 7C illustrates an electron microscopy image of an example of the contact sites of an exemplary adhered HUVEC cell on a nano-roughened PMMA substrate, consistent with one or more exemplary embodiments of the present disclosure.
Figure 7D:
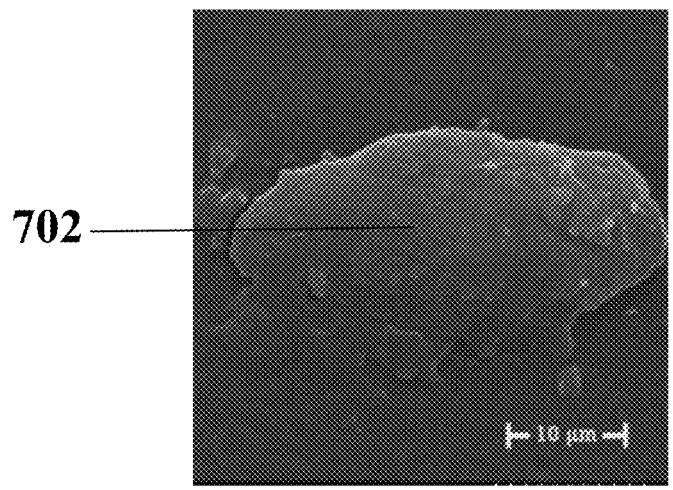
FIG. 7D illustrates an electron microscopy image of an example of the contact sites of an exemplary adhered HUVEC cell on a smooth PMMA substrate, consistent with one or more exemplary embodiments of the present disclosure.

FIGS. 7C and 7D show exemplary electron microscopy images of an example of the contact sites of an exemplary adhered HUVEC cell 701 on a nano-roughened PMMA substrate (FIG. 7C) and an exemplary adhered HUVEC cell 702 on a smooth PMMA substrate (FIG. 7D). It may be observed that the nano-indentations may enhance the hydrophobicity of the surface and increase the contact sites between cell 701 membrane and substrate which may result in an improved adhesion of the cells 701 on the surface of the PMMA without requirements to any adhesive proteins (FIG. 7C). HUVEC cell 702 may exhibit a lower extension with reduced contact sites on the smooth surface (FIG. 7D).

Example 2: Fabricating a Biosensor with a PDMS/Glass Substrate

In this example, an example of the biosensor 201 was fabricated. The fabricated exemplary biosensor was included 16 single parallel microelectrodes, each equipped with a single consecutive metastatic cell sensing traps (a single HUVEC) that was selectively covered whole of the microelectrode by DEP patterning. The biosensor width was about 100 μm and the volume of the cavity including reservoir was about 200 μl.

For mold fabrication, a SU-8 photoresist spun on a silicon wafer was patterned in the form of microfluidic channels through a chrome photomask by a conventional photolithography technique. Poly(dimethylsiloxane) (PDMS) prepolymer and cross-linker (Sylgard 184) were mixed with a 10:1 ratio and the obtained mixture was poured on the mold, first degassed, and then cured at about 65° C. for at least about 4 hours. The biosensor was built by bonding the cured PDMS peeled off from the mold and a glass substrate after surface activation in oxygen plasma. The fabricated biosensor was primed by flushing ethanol through microfluidic channels and then washed using deionized water and PBS before use.

A procedure for cell patterning based on DEP was Applied to obtain a selective and viable pattern of single HUVECs just on the sensing traps. First, HUVECs were suspended in an EGTA-containing DEP buffer and flown into the cavity of the fabricated biosensor with a rate of about 5 μL/min. Then, an AC signal (about 5 Vpp, about 5 MHz) was applied to the sensing microelectrodes to generate p-DEP forces to guide cells on the array of traps during the cell seeding process, shaking the chip during cell patterning may suppress from the physical attachment of the cells in non-desired places. Moreover, a calcium-containing DEP buffer without EGTA (about 0.75 mM $CaCl_2$; pH of about 7.0, about 305 Osm, about $2.74\times10^{-2}$ S/m) may be injected at about 5 μL/min to improve the detachment of non-patterned cells. Subsequently, the AC. turned off after the HUVECs were patterned singularly on sensing traps, DMEM with about 10% FBS and about 1% penicillin/streptomycin was injected at about 5 μL/min to replace the calcium-containing DEP buffer. The exemplary time lapse optical images that were taken from the patterning process indicated that the spread of each of the HUVECs on a single traps was about 4 hours. Finally, the HUVECs-covered microelectrodes were measured by an electrical readout system to be ensure from the blocking of each sensing region by a HUVEC trap. Then, the biosensor and the corresponding system may be ready to be interacted by a biopsied sample of a patient.

As the cells are more polarizable than the surrounding media, the dipoles induced in the cells may be aligned parallel to the applied electric field. The field may be spatially non-uniform and the maximums may be occurred on the microelectrodes patterned on the surface of the biosensor. So a resultant force due to DEP may pull the cells towards field maxima.

When the polarity of the applied field was reversed, DEP continued to pull the HUVEC towards the field maximum, allowing AC operation at high frequencies to reduce electrical loading of the cell membrane. After trapping a single HUVEC at the maximum region of the field, existed on the sensing region of microelectrodes, the media solution was flowed across the surface as a destabilizing force to remove the additional cells might be trapped on non-desired places to implement the position of single HUVECs just on the sensing electrodes. The applied flows were powerful enough to remove the additional cells but too weak to remove the strongly trapped cell directly above each electrode.

Figure 8A:
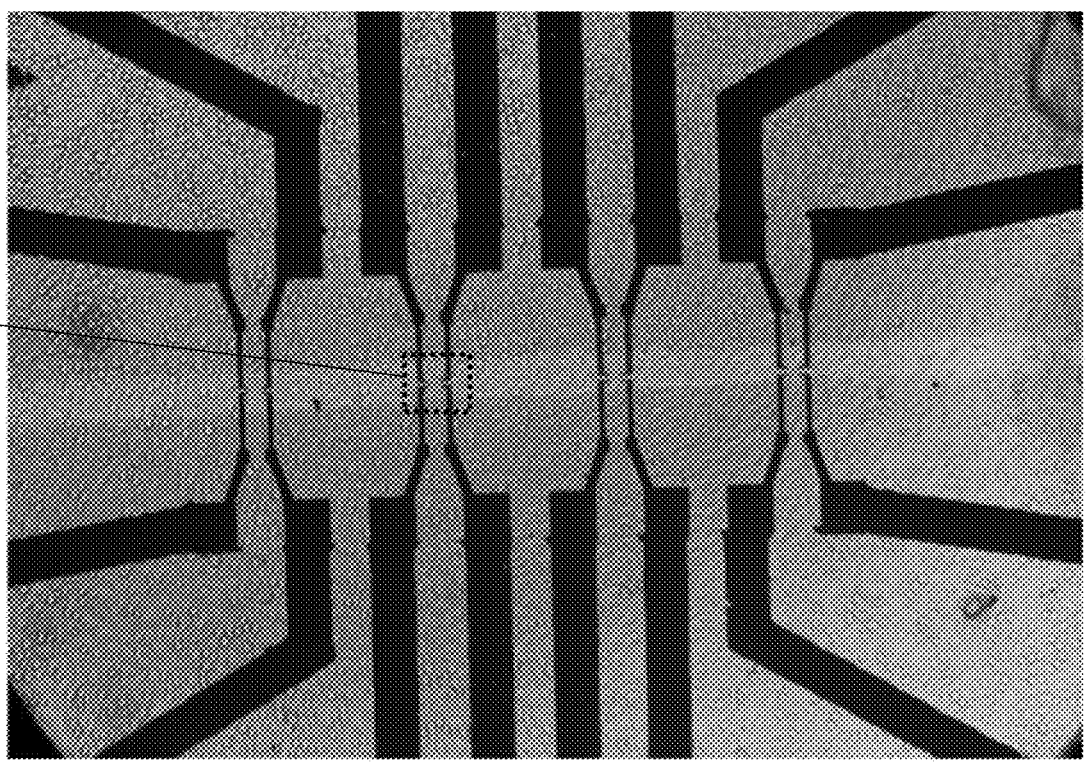
FIG. 8A illustrates an image of the surface of an exemplary biosensor fabricated according to a method in accordance with EXAMPLE 1, consistent with one or more exemplary embodiments of the present disclosure.

FIG. 8A shows an image of the surface of an exemplary biosensor 201 fabricated according to the present example. The configuration of the 16 microelectrodes 208 may be observed in this figure. The size of the main detecting biosensor region may be about 0.5×0.5 $cm^2$. Each couple of electrodes 208 with a size of about 10 µm and a distance of less than about 10 µm were repeated in multiple rows for redundancy.

Figure 8B:
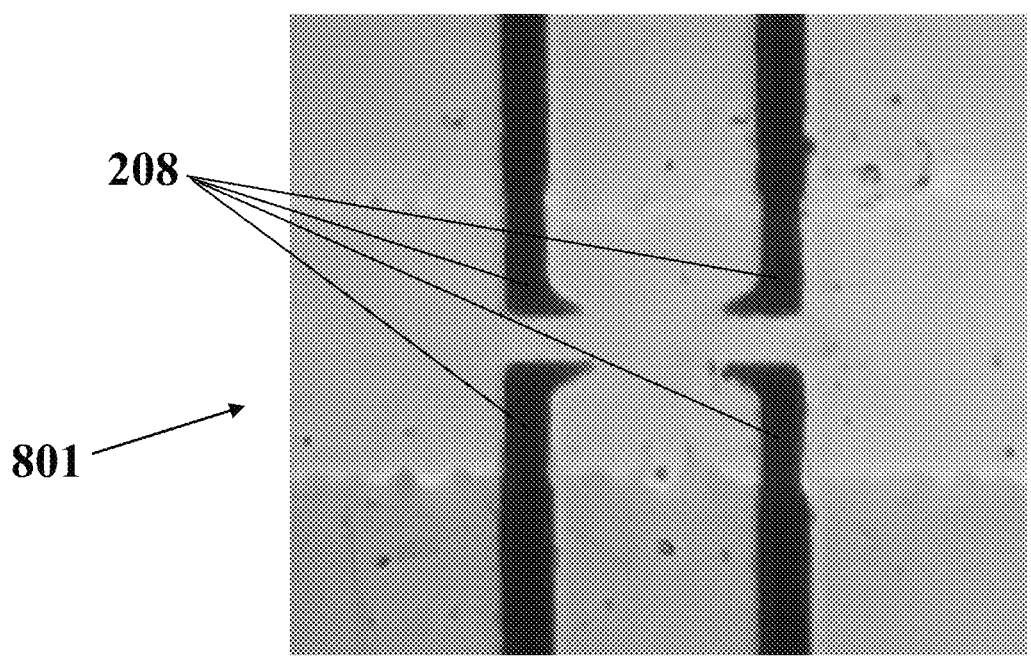
FIG. 8B illustrates an image a magnified portion of the surface of an exemplary fabricated biosensor before adding a solution of HUVECs accordance with EXAMPLE 1, consistent with one or more exemplary embodiments of the present disclosure.

FIG. 8B shows an image of a magnified portion 801 (in FIG. 8A) of the surface of an exemplary biosensor 201 before adding a solution of HUVECs and DEP forcing that fabricated according to the present example. The microelectrodes 208 are represented in this figure.

Figure 8C:
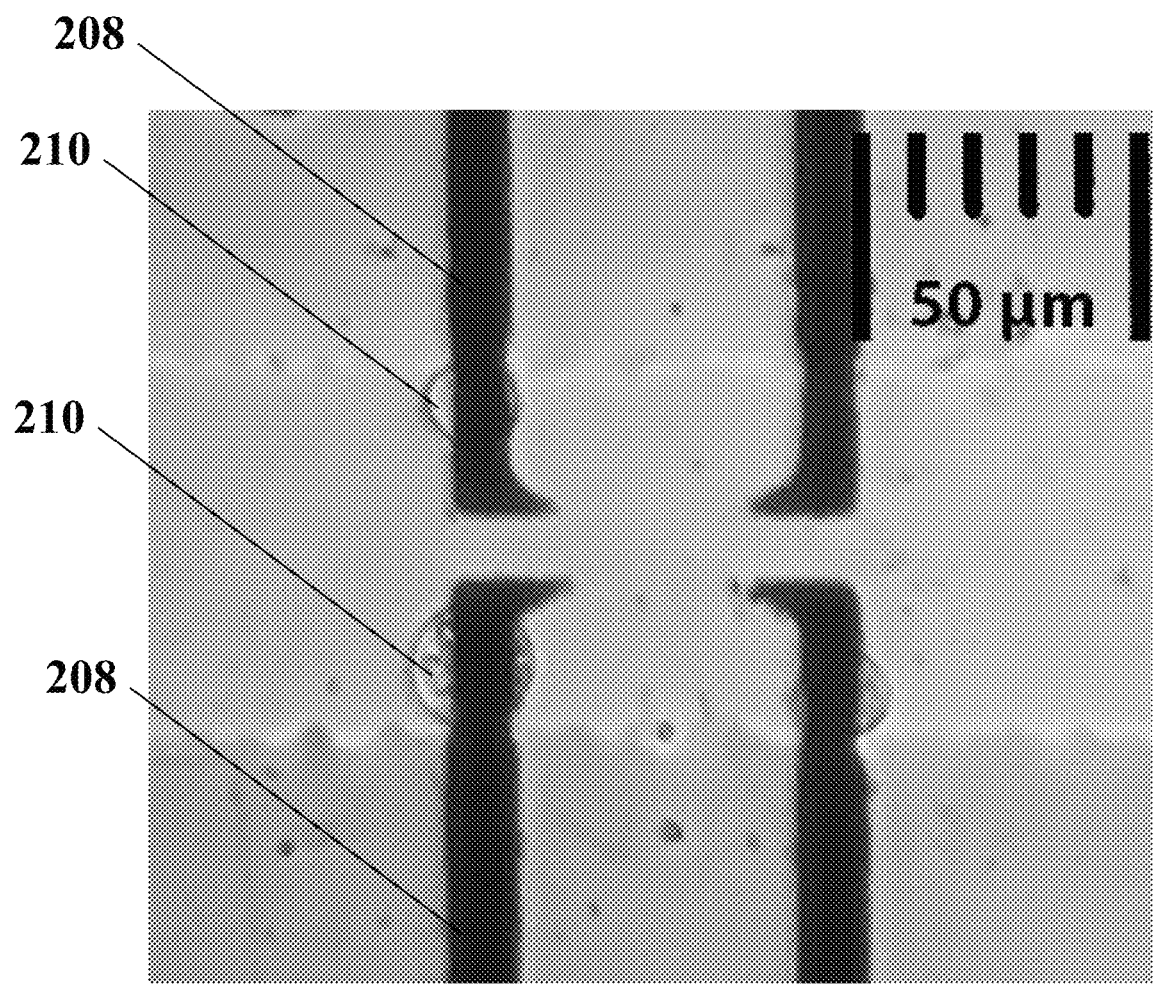
FIG. 8C illustrates an image a magnified portion of the surface of an exemplary fabricated biosensor at about 27 min after applying DEP on an added solution of HUVECs in accordance with EXAMPLE 1, consistent with one or more exemplary embodiments of the present disclosure.

FIG. 8C shows an image of the magnified portion 801 of the surface of an exemplary biosensor 201 that was fabricated according to the present example at about 27 min after DEF forcing on the added solution of HUVECs to the biosensor. This figure represents the HUVECs 210 that may be covered the microelectrodes 208. It may be observed that the single HUVECs 210 were selectively covered each electrical trap (microelectrdoes 208), which was achieved by electrophoretic process (electrostatic driving force biased on the system).

Example 3: Biosensor Characterization and Optimization Using Cell Lines

In this example, an exemplary system and method were utilized to diagnose metastatic cell lines. Accordingly, an array of individual sensing traps including an array of microelectrodes, each microelectrode covered by a single HUVEC, was used to investigate the non-metastatic cell lines (MCF7) and metastatic cell lines from breast cancers (MDAMB468).

Cell Lines Culture:

MCF7 cell lines isolated from grade I of human breast tumors and MDA-MB468 cell lines isolated from grade IV of human breast tumors were obtained from the standard cell banks of the National cell bank of Iran (NCBI). These obtained cell lines were maintained at a temperature of about 37° C. (in about 5% $CO_2$, about 95% air) in a RPMI-1640 medium or a DMEM medium supplemented with about 5% fetal bovine serum and about 1% penicillin/streptomycin. The fresh medium was replaced every other day. In exemplary diagnosis tests for cell lines, the metastatic cancerous cells (MDA-MB468 cell lines) and primary cancerous cells (MCF7 cell lines) were individually added (by the concentration of about 1/10 versus endothelial cells) to each HUVEC covered sensing wells after culturing the HUVECs on the surface of the biosensor. Then, electrical impedance as well as optical images of the sensors were recorded in time lapses. All cell lines were tested and found negative for a *Mycoplasma* contamination. The cells were detached from the plates by trypsin and counted by a neobar laam.

Metastatic Cell Lines Diagnosis

An analytical version of the fabricated biosensor with 16 single sensing-trapping electrodes was used herein. The electrical impedance of single HUVEC covered sensing traps was measured at a frequency of about 4 kHZ. Rare concentrations (50 cells #/ml) of MDA-MB 468 and MCF-7 cells were separately introduced into the cavity of two individual biosensors. The biosensor was covered by a mixed solution of 5 MDAMB468 and 50000 MF10 breast cells.

Figure 9A:
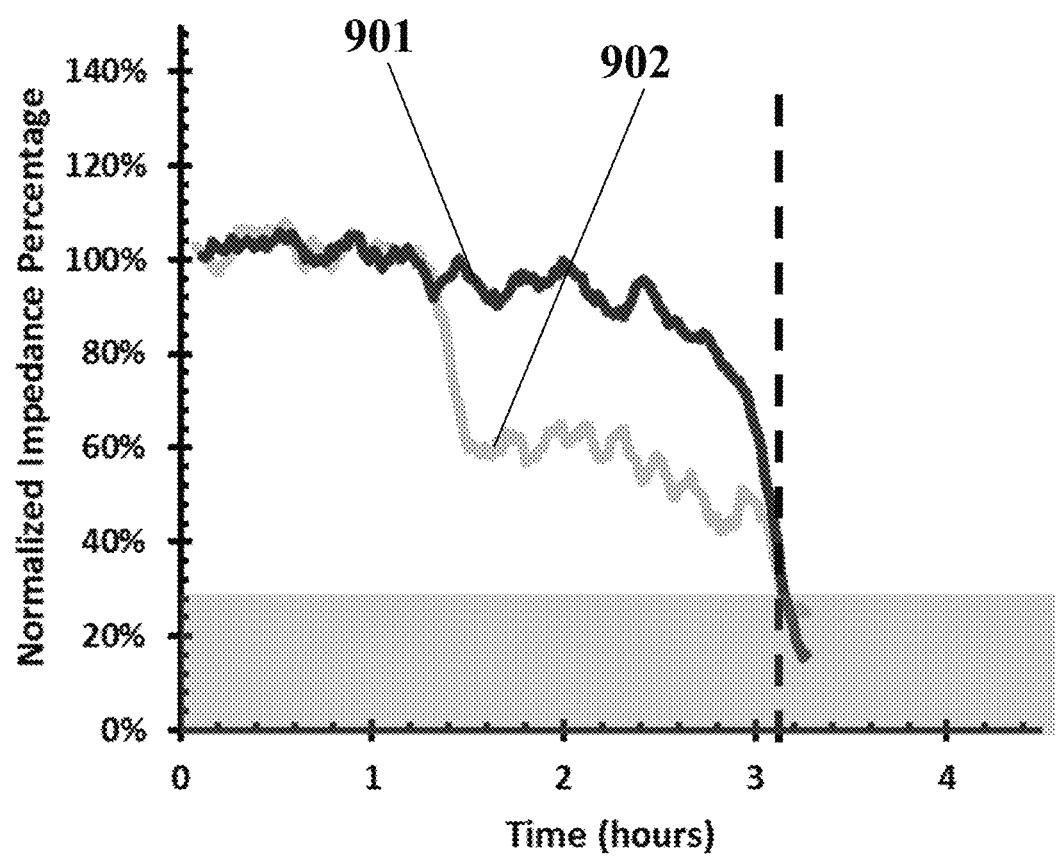
FIG. 9A illustrates an example time-lapse electrical impedance curve for two exemplary microelectrodes of an example biosensor diagnosing exemplary metastatic MDA-MB 468 cell lines, consistent with one or more exemplary embodiments of the present disclosure.
Figure 9B:
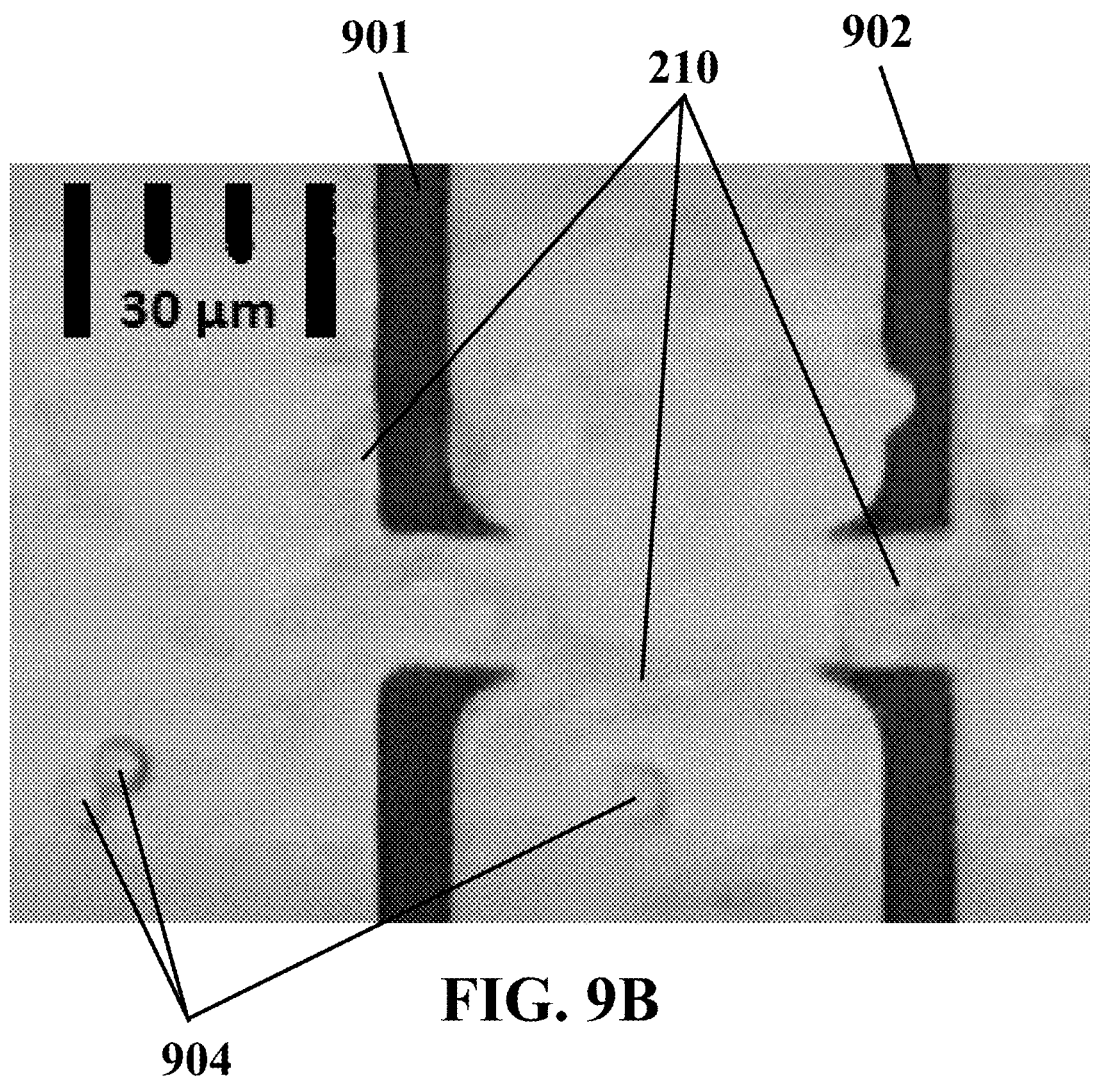
FIG. 9B illustrates an example optical image of two exemplary microelectrodes of an example biosensor diagnosing exemplary metastatic MDA-MB 468 cell lines, consistent with one or more exemplary embodiments of the present disclosure.
Figure 9C:
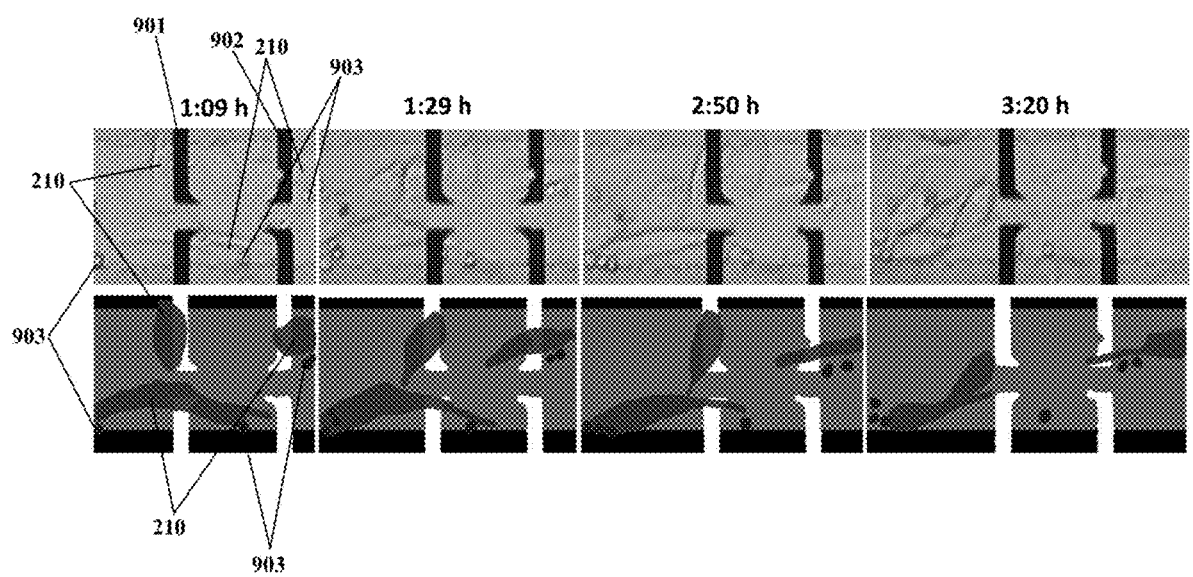
FIG. 9C illustrates an example of time-lapse optical images of two exemplary metastatic cell traps of an example biosensor diagnosing exemplary metastatic MDA-MB 468 cell lines during about 3:20 hours after introducing the metastatic cells, consistent with one or more exemplary embodiments of the present disclosure.

FIGS. 9A-C show the optical-electrical results for the metastatic MDA-MB 468 cell lines. FIG. 9A shows an example time-lapse electrical impedance for two exemplary microelectrodes 901 and 902 (designated in FIG. 9B) during about 3 hours and 20 min after introducing the metastatic cells 903 onto the fabricated and used biosensor, consistent with one or more embodiments of the present disclosure. Individual cells have a width less than about 10 µm and the sensing electrodes covered by single HUVECs have a width more than about 15 µm wide. FIG. 9B shows an example captured image at about 36 min after introducing the metastatic cells 904 onto the fabricated and used biosensor, consistent with one or more embodiments of the present disclosure. FIG. 9C (top) shows an exemplary set of time-lapse images corresponding to FIG. 9A including a set of images taken at 1:09 hours, 1:29 hours, 2:50 hours and 3:20 hours after introducing the metastatic cells 903. Moreover, FIG. 9C (bottom) illustrates a schematic set of images respective to those at the top of this figure for more clarifying of the MDA-MB 468 cell's 903 invasion to the HUVECs 210. It may be observed from these figures that MDA-MB 468 cells 903 invaded HUVEC traps 210 and retracted the HUVEC traps 210 from the surface of the electrodes in less than about 3.5 hours and lowered the electrical response of the single sensing trap to 0.2 of the initial value. Even presence of two metastatic MDA-MB468 cells 903 induced electrical spike response in a sensing trap. This might be correlated with the strong tendency of metastatic cells 903 to invade the HUVECs 210 layer. Live matching (between electrical response and optical image) system of the disclosed system may elaborate the time correlation between the metastasis induced HUVEC retraction and significant reduction in electrical response of the traps. It should be noted that the forces acting on the HUVEC traps 210 just have been initiated from metastatic attraction of cancer cells as no drag forces no fluid flow, and no reaction forces applied from the system.

Figure 10A:
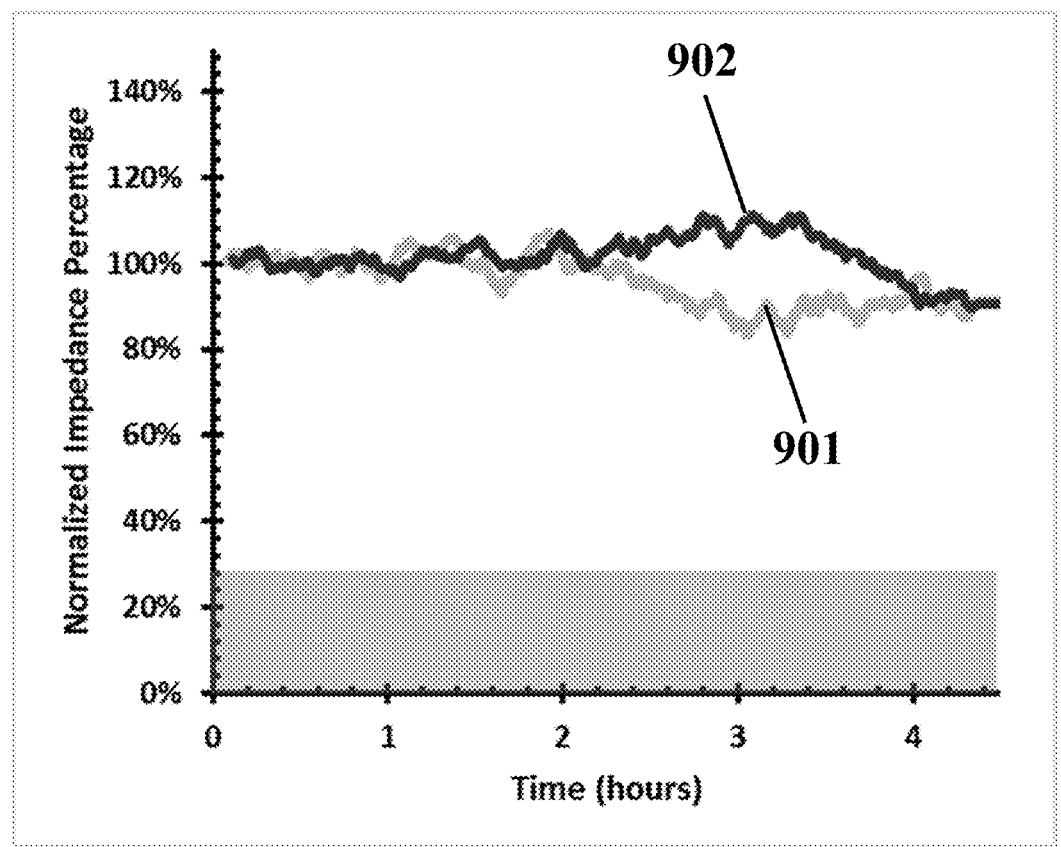
FIG. 10A illustrates an example time-lapse electrical impedance curve for two exemplary microelectrodes of an example biosensor for exemplary MCF-7 cell lines, consistent with one or more exemplary embodiments of the present disclosure.

In contrast, MCF-7 cells didn't present any aggressive interactions by HUVEC sensing traps 210 and no changes in the electrical response was observed. FIG. 10A shows an example time-lapse electrical impedance for two exemplary microelectrodes 901 and 902 (designated in FIG. 10B) during about 4 hours and 30 min after introducing the MCF-7 cells 1001 onto the fabricated and used biosensor, consistent with one or more embodiments of the present disclosure.

Figure 10B:
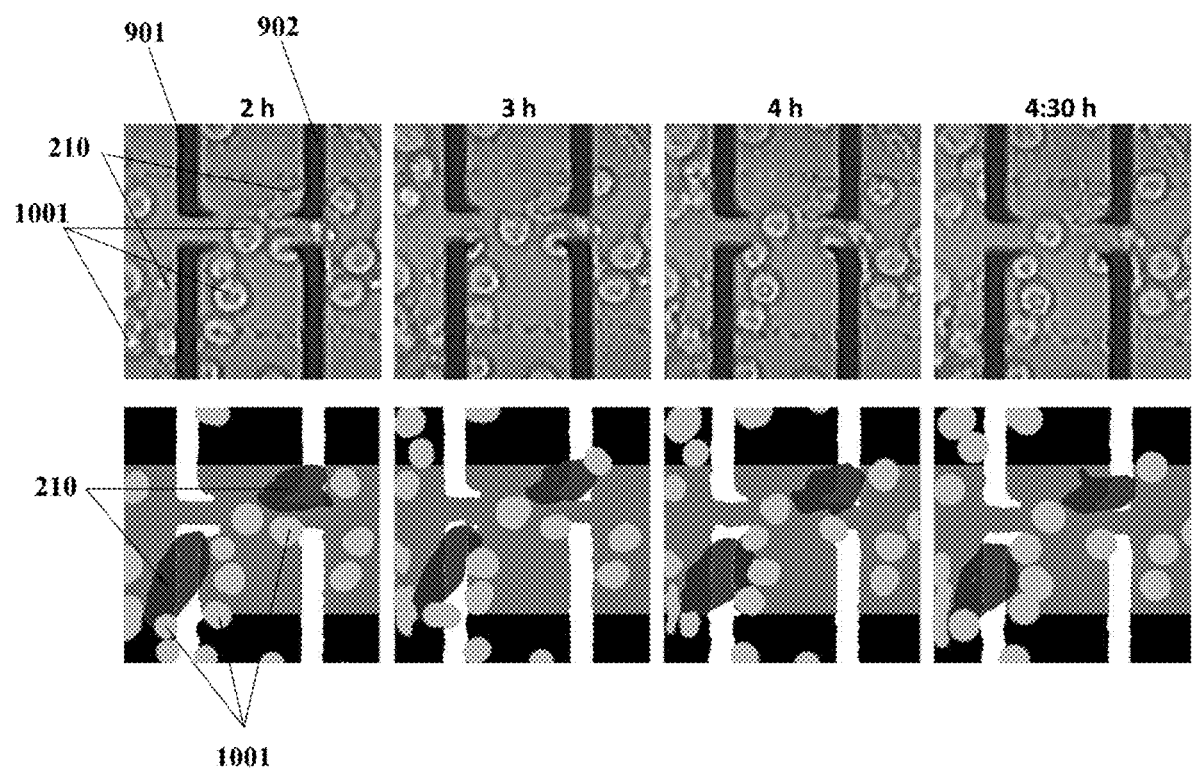
FIG. 10B illustrates an example of time-lapse optical images of two exemplary metastatic cell traps of an example biosensor diagnosing exemplary MCF-7 cell lines during about 4.5 hours after introducing the MCF-7 cells, consistent with one or more exemplary embodiments of the present disclosure.

FIG. 10B shows a set of images captured at 2 hours, 3 hours, 4 hours, and 4.5 hours after introducing the MCF-7 1001. According to these figures, no invasive interaction was observed and recorded for MCF-7 cells in similar time. Cells 1001 just attach beneath the HUVEC traps 210 but neither retract them nor induce reductive electrical spikes. HUVECs 210 maintained their primary location with minor fluctuation during about 4.5 hours after addition of MCF-7 cells 1001.

Finally, after about 5 hours from the introduction of the cell solution to the individual devices, the exemplary disclosed system captured 4/5 MDA-MB-468 cells and 0/200 of MCF-7 cells in a great match between HUVECs retraction from the electrodes (recorded by the microscope optical unit) and significant reduction in the electrical response (measured by the electrical signal extraction board).

Example 4: Identification of Invasive/Metastatic Cells in Biopsied Samples of Patients In this example, an exemplary system and method was applied to Core needle biopsied samples collected by interventional radiologist from the breast tumor and sentinel lymph nodes of 20 patients (19 females and 1 male) with breast cancers. Moreover, additional sample study were done on surgically removed samples of some patients (2/20). Minor part of each sample was tested by an exemplary fabricated biosensor and the major part was prepared in parallel for pathological assays including H&E, IHC and RT-PCR methods. About 4-5 hours after live recording the optical and electrical data, the presence of metastatic/invasive cells in the lymph/tumor sample could be detected or diagnosed by the exemplary system.

Figure 11A:
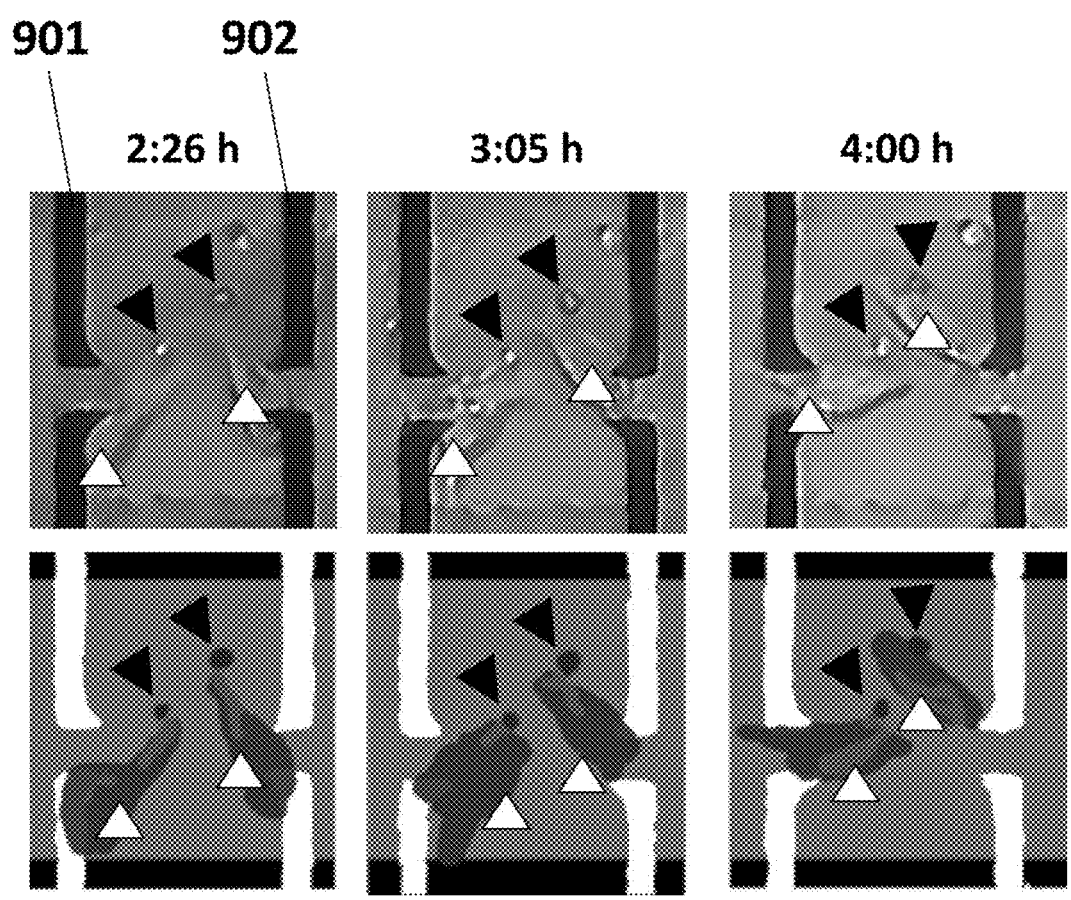
FIG. 11A illustrates exemplary set of optical images (top) and the corresponding schematics (down) of two exemplary live metastatic cells (ID: 1, designated by ▼) detached from an isolated lymph of a patient and attacking two individual single HUVEC sensing traps (designated by Δ), consistent with one or more exemplary embodiments of the present disclosure.
Figure 11B:
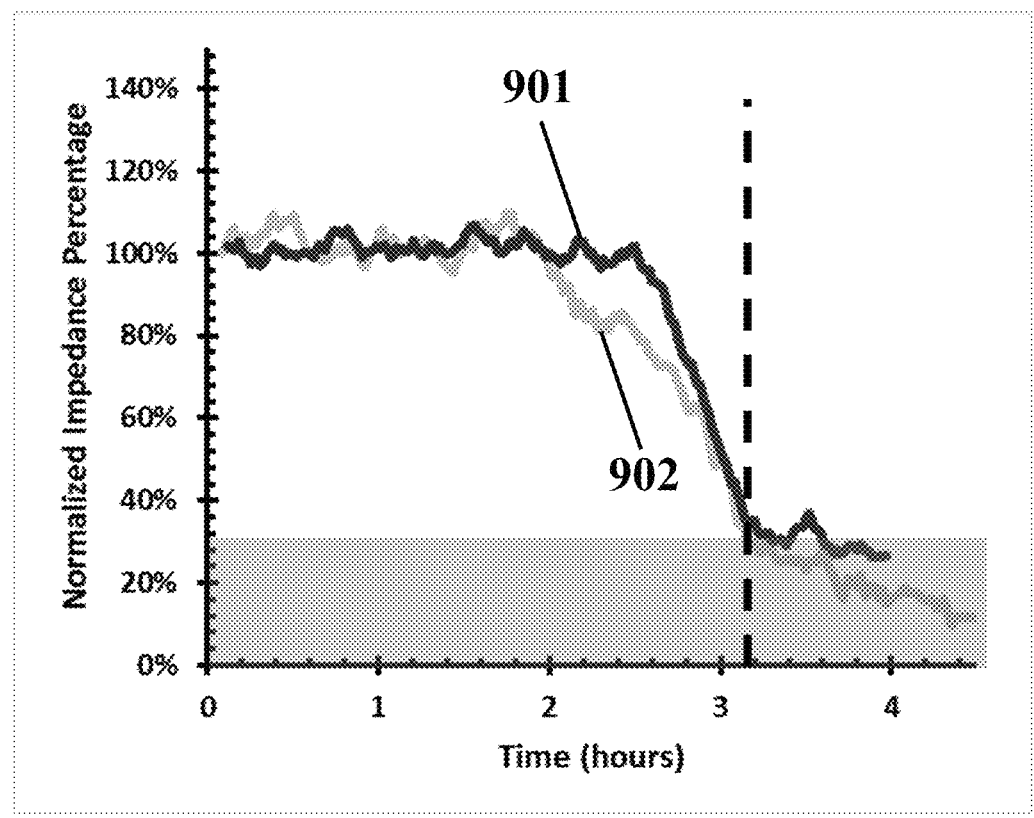
FIG. 11B illustrates an example trend of time-lapse electrical responses of two example of electrodes covered by two exemplary HUVECs invaded by two exemplary metastatic cells (ID: 1), consistent with one or more exemplary embodiments of the present disclosure.

FIGS. 11A and 11B show exemplary capturing and diagnosis of exemplary metastatic cells (designated by ▼) in SLN samples of a patient with metastatic cancer (resected by CNB) by disclosed system and methods. It may be observed that a representative live metastatic cell, detached itself from the biopsied SLN sample of a patient (with metastatic breast cancer: ID1) invading to a HUVEC sensing trap (designated by Δ) and subsequent retracting it from the electrodes in less than about 4.5 hours (FIG. 11A). As a result, the disclosed system may report a considerable reduction in an electrical response of two invaded traps 901 and 902 (FIG. 11B). This matching could be observed in simultaneous images derived from the optical captures. It is worth noting that time-lapse images of all of the individual traps exhibited reductive spikes were captured during the metastatic interaction. So the patient was scored as positive for metastasis.

Figure 11C:
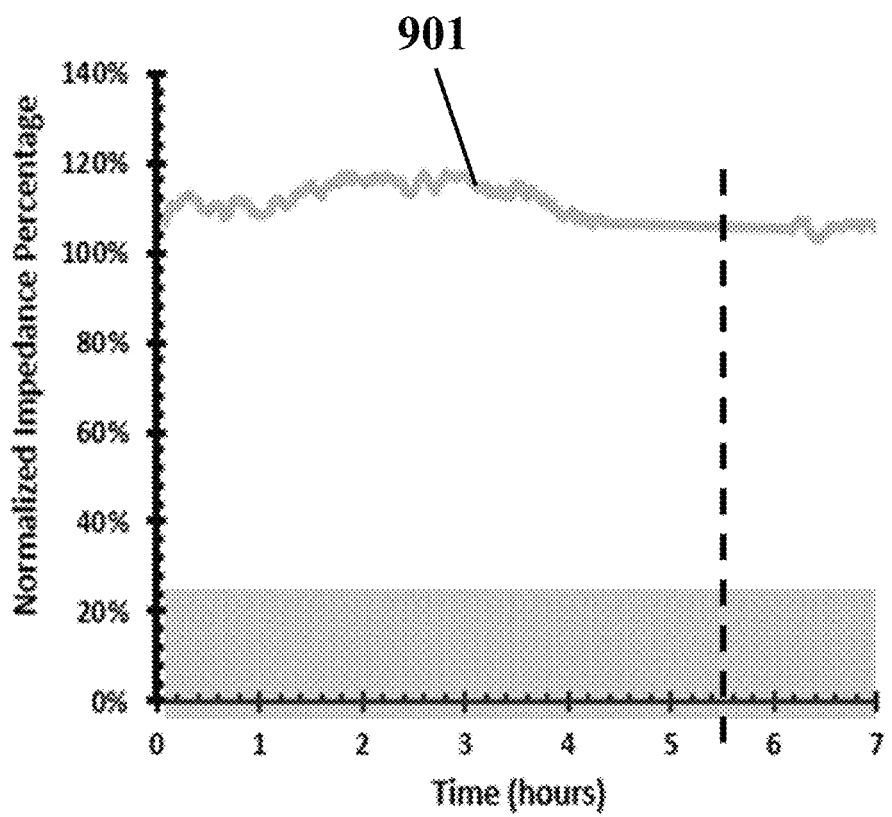
FIG. 11C illustrates an example trend of time-lapse electrical responses of one example electrode covered by HUVECs remain non-invaded by exemplary non-metastatic cells (ID: 15), consistent with one or more exemplary embodiments of the present disclosure.

FIG. 11C shows an example set of time-lapse electrical responses curve for an exemplary sensing trap 901 for the patients those were diagnosed as negative lymph nodes (ID: 15), in which none of the detached cells from the biopsy samples invaded to the HUVEC single traps so that no significant changes were observed in the recorded electrical impedance.

Figure 12A:
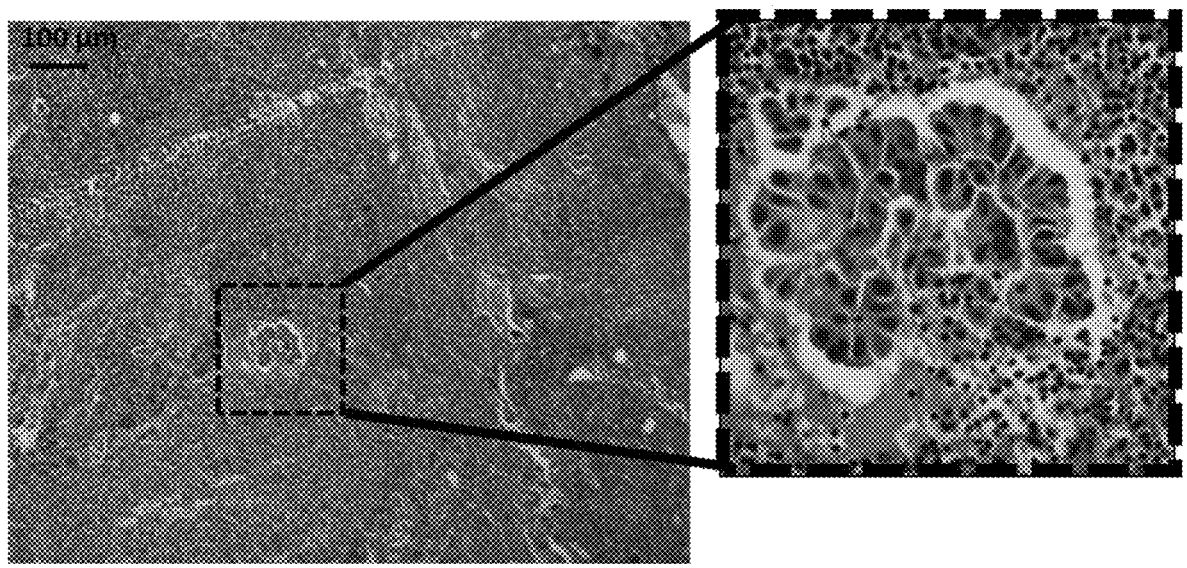
FIG. 12A illustrates an exemplary H&E resulted image of the patient ID: 1 sample having a metastatic cancer, consistent with one or more exemplary embodiments of the present disclosure.
Figure 12B:
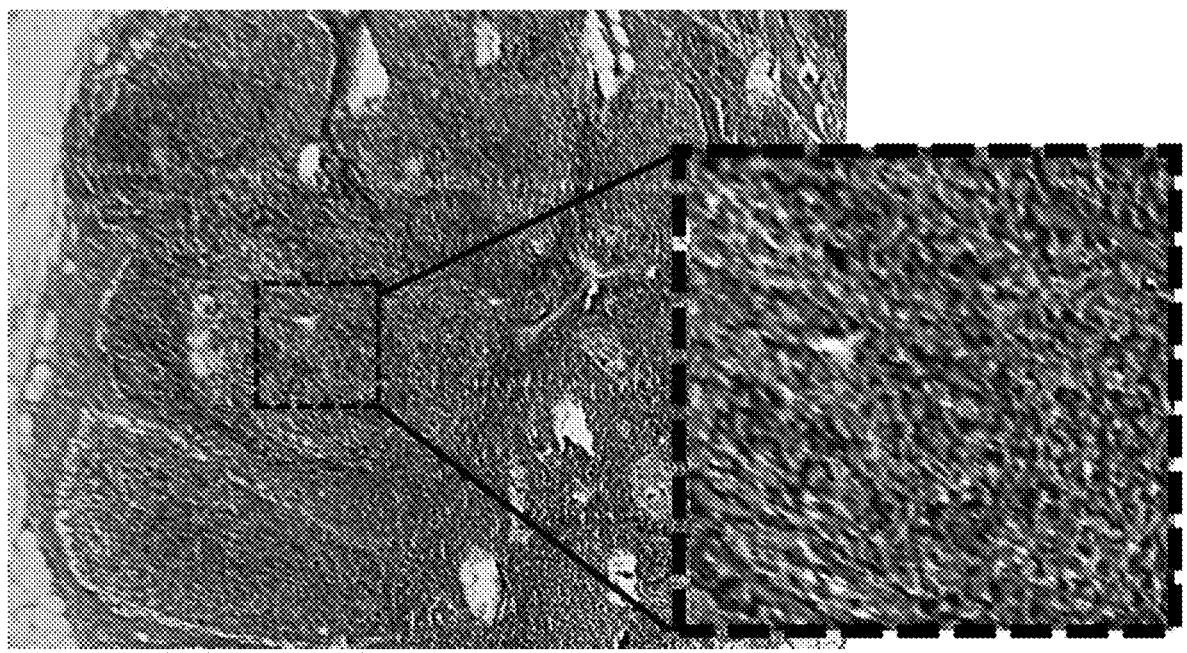
FIG. 12B illustrates an exemplary H&E resulted image of the patient ID: 15 sample having a non-metastatic condition, consistent with one or more exemplary embodiments of the present disclosure.

In addition, a standard diagnostic method Hematoxylin-Eosin (H&E) staining was applied on the 20 samples from the 20 patients to compare with the results obtained by applying the disclosed system and method. FIGS. 12A and 12B show exemplary H&E images of the sentinel lymph nodes of the patients ID: 1 (FIG. 12A) and ID: 15 (FIG. 12B). It may be observed from the H&E images of the sentinel lymph nodes of the patient ID: 1 that the Nest of tumoral cells with hyperchromic nuclei was distinguishable in lymph node structure. Such result corroborated the correct detection of metastasis in this patient by the disclosed system and method. Referring to FIG. 12B, H&E results indicated reactive lymphoid hyperplasia without any signs of malignancy for patient ID: 15.

Comparing the results from the present bio-chip, system and method with those from H&E tests showed that all of the lymph node 20 samples biopsied from the patients with metastatic cancers based on the H&E diagnosis (ID: 1 to ID: 12) were shown with sensing traps capture of metastatic cells by the disclosed system and method. Moreover, all of the biopsied breast tumors diagnosed as invasive carcinoma in H&E, exhibited invasion to at least one sensing trap in the set of optical images.

But, the bio-chip captured metastatic cells in the lymph node samples of 3/20 patients (patents ID: 18, 19 and 20) diagnosed as invasive carcinoma without any lymph node metastasis by H&E methods. Hence, these patients were assumed as doubtful people to metastatic cancer. In this regard, the patients were categorized in three groups due to the results of their lymph node assay by H&E and the bio-chip; G1: known metastatic cases (positively scored by both H&E and bio-chip), G2: known safe lymph nodes (negatively scored by both H&E and bio-chip) and G3: doubtful cases (negatively scored by H&E but positively scored by bio-chip). No patient was observed with negative score in bio-chip and positive score in H&E. These three groups and the corresponding data are shown in Table 1.

Immunohytochemical (IHC) and Molecular Analysis (RT-PCR) of Patients

To test the versatility of the bio-chip for accurate addressing the presence of metastatic cells in core needle biopsied SLNs, immunohistochemical markers of metastatic cells were applied on the samples through an IHC assay as a more advanced staining technique. IHC may be employed to investigate the earliest changes in transformed tissues, identifying metastatic associated cellular changes might not normally visible with H&E. To be ensure from the micro-metastasis, presence of the cells expressed PCK and Vimentin were deeply investigated by preparing multi-level IHC from the SLNs of the patients from all groups with special consideration on group G3 (doubtful patients).

Table 1 shows the IHC results of SLNs in all patients. Expression of PCK and Vimentin in SLNs of the known metastatic cases (G1) confirmed the correlated diagnosis of both bio-chip and H&E for those patients (patients ID: 1-12). Also, negative expression of PCK and Vimentin in the SLNs of the known non-metastatic cases (G2) supported their safe lymph nodes as indicated by both bio-chip and H&E (patients ID: 13-17). It is worth noting that the trace of tumor cells expressed PCK and Vimentin was identified in SLNs of all G3 patients (patients ID 18, 19 and 20). Such results revealed the presence of metastasis in doubtful patients which had been diagnosed by bio-chip. The cells in epithelial to mesenchymal transition, would express both the PCK and Vimentin simultaneously which would be the first signature of micrometastasis. Most micro metastasized breast cancer cells might appear to exist in a hybrid epithelial-mesenchymal state, a phenotype observed in instances of breast circulating tumor cells and consistent with the possibility of trans-endothelial (metastatic) migration. Other point was that following one of the doubtful patients (patient ID: 20), after the surgical resection of the lymph node (due to the surgeon's opinion), indicated the involvement of 1/10 lymph's frozen sections to malignant cells in H&E image. This is a hopeful achievement that detecting a metastatic case from the lymph CNB sample before any pathological analysis would be possible by the bio-chip.

Also, RT-PCR tests were investigated on the patients from all of three groups. Analysis of the results (Table 1) may show that: (i) All of the lymph nodes extracted from the G1 patients, expressed detectable levels of transcripts encoding metastatic associated proteins (such as Vim, MMP2&9 and N-Cadherin) in comparison with a normal lymph sample. (ii) The primary breast tumor assayed in some of these patients (Patients ID: 1-3) expressed high levels of N-Cadherin (iii) 4/5 patients in G2 didn't express Vim. Moreover, very Low expression of N-Cadherin and MMP9 as well as low expression of MMP2 were observed in the SLNs of all G2 samples. Significant expression of N-Cadherin in tumor samples assayed in 3 patients from G2, revealed the invasive state of the breast tumors similar to G1 (iiii) All three patients from G3 (doubtful cases) expressed detectable levels of Vim as well as meaningful levels of MMP2&9. Expression of N-Cadherin was significant in one sample (Patient ID: 19) meanwhile it was minor in two others (Patients ID: 18 and 20). Trace of N-Cadherin was significant in the breast tumor samples of the patients from G3. The mentioned results of RT-PCR in doubtful patients indicated the trace of metastasis in their SLNs as another support to the precise diagnosis of bio-chip.

The impact of bio-chip in detecting the metastasis in the samples which could be hardly diagnosed even by IHC and RT-PCR may be observable. The low shear stress of the metastatic cells and biochemical signals received from vascular cells, facilitate the detachment of metastatic cells from original biopsied tissue to invade the sensing traps of bio-chip in less than about 5 hours.

TABLE 1

The bio-chip, H&E, IHC and RT-PCR diagnostic results of breast tumors & SLNs removed from breast cancer patients by CNB. Detection of metastasis in each assay is correlated with expression levels of transcripts associated with the presence of malignancy in the lymph region such as Vim, N-Cad, MMP2, and MMP9.

| Patient ID | Bio-Chip | H&E metastasis | IHC | | RT-PCR | | | |
|---|---|---|---|---|---|---|---|---|
| | | | Vim | PCK | Vimentin | N-Cadherin | MMP2 | MMP9 |
| 1 | ☐ | ☐ | ☐ | ☐ | 41.26 | 15.64 | 15.11 | 17.66 |
| 2 | ☐ | ☐ | ☐ | ☐ | 12.84 | 38.05 | 11.5 | 15.7 |
| 3 | ☐ | ☐ | ☐ | ☐ | 18.28 | 21.11 | 19.77 | 8.32 |
| 4 | ☐ | ☐ | ☐ | ☐ | 15.076 | 32.85 | 9.95 | 15.23 |
| 5 | ☐ | ☐ | ☐ | ☐ | 42.81 | 28.23 | 13.97 | 8.65 |
| 6 | ☐ | ☐ | ☐ | ☐ | 40.98 | 22.43 | 17.09 | 9.78 |
| 7 | ☐ | ☐ | ☐ | ☐ | 13.43 | 20.62 | 6.59 | 9.15 |
| 8 | ☐ | ☐ | ☐ | ☐ | 56.84 | 28.92 | 8.01 | 10.26 |
| 9 | ☐ | ☐ | ☐ | ☐ | 28.56 | 31.58 | 11.41 | 13.46 |
| 10 | ☐ | ☐ | ☐ | ☐ | 42.75 | 27.55 | 6.42 | 18.18 |
| 11 | ☐ | ☐ | ☐ | ☐ | 25.79 | 36.4 | 17.85 | 7.47 |
| 12 | ☐ | ☐ | ☐ | ☐ | 11.48 | 27.41 | 11.18 | 17.68 |
| 13 | ☐ | ☐ | ☐ | ☐ | 0.0091 | 2.03 | 2.6 | 0.53 |
| 14 | ☐ | ☐ | ☐ | ☐ | 0.49 | 1.11 | 3.76 | 0.5 |
| 15 | ☐ | ☐ | ☐ | ☐ | 0.12 | 0.83 | 1.77 | 0.28 |
| 16 | ☐ | ☐ | ☐ | ☐ | 0.32 | 0.97 | 1.56 | 0.26 |
| 17 | ☐ | ☐ | ☐ | ☐ | 0.83 | 2.12 | 2.11 | 0.46 |
| 18 | ☐ | ☐ | ☐ | ☐ | 3.16 | 2.5 | 18.25 | 11.47 |
| 19 | ☐ | ☐ | ☐ | ☐ | 4.84 | 14.25 | 15.28 | 2.21 |
| 20 | ☐ | ☐ | ☐ | ☐ | 2.04 | 1.22 | 5.32 | 6.91 |

What is claimed is:

1. A method for fabricating a biosensor for metastasis diagnosis, comprising:

coating a photoresist layer on a substrate layer;

forming a patterned region by patterning the photoresist layer utilizing a photolithography process;

forming a nano-roughened patterned region by forming a plurality of nano-features on the patterned region;

stripping the photoresist layer from the substrate layer;

forming an array of microelectrodes and an array of electrical connections on the nano-roughened patterned region by depositing a gold/titanium (Au/Ti) bilayer on the substrate layer with the nano-roughened patterned region, each electrical connection of the array of electrical connections corresponding to a respective microelectrode of the array of microelectrodes; and forming a metastatic cell sensing trap on at least one microelectrode of the array of microelectrodes, comprising:

placing a solution of Human Umbilical Vein Endothelial Cells (HUVECs) on the biosensor; and forcing an attachment between at least one HUVEC of the HUVECs and at least one microelectrode of the array of microelectrodes on the biosensor.

2. The method of claim 1, wherein coating the photoresist layer on the substrate layer comprises spin coating the photoresist layer on the substrate layer.

3. The method of claim 1, wherein coating the photoresist layer on the substrate layer comprises coating the photoresist layer on the at least one of a Poly(methyl methacrylate) (PMMA) layer and a glass layer.

4. The method of claim 1, wherein forming the patterned region comprises patterning the photoresist layer with a pattern comprising one of a regular pattern for arrangement of the array of microelectrodes and a non-regular pattern for arrangement of the array of microelectrodes.

5. The method of claim 4, wherein the regular pattern comprises one of a parallel arrangement for the array of microelectrodes and a circular arrangement for the array of microelectrodes.

6. The method of claim 5, wherein the parallel arrangement for the array of microelectrodes comprises a plurality of couple electrodes placed parallel to each other, each couple electrodes comprising:
  a first electrode; and
  a second electrode located at the bottom of the first electrode,
  wherein a distance between the first electrode and the second electrode is less than 10 μm.

7. The method of claim 5, wherein the circular arrangement for the array of microelectrodes comprises:
  an electrical ground comprising a circular electrode at a center of the patterned region; and
  a plurality of circular electrodes located around the electrical ground.

8. The method of claim 5, wherein the circular arrangement for the array of microelectrodes comprises a plurality of couple circular electrodes with a circular arrangement, each couple electrodes comprising:
  a first circular electrode; and
  a second circular electrode located adjacent to the first electrode,
wherein a distance between the first electrode and the second electrode is less than 10 μm.

9. The method of claim 1, wherein forming the plurality of nano-features on the patterned region comprises:
  placing the substrate with the patterned region in a reactive ion etching (RIE) system; and
  processing the patterned region by $SF_6$, $H_2$ and $O_2$ gases in the presence of radiofrequency (RF) Plasma.

10. The method of claim 1, wherein forming the plurality of nano-features on the patterned region comprises forming a plurality of nano-sized hills on the patterned region with a width of less than 80 nm and a depth of less than 120 nm for each respective hill of the plurality of nano-sized hills.

11. The method according to claim 1, wherein depositing the bilayer of Au/Ti on the substrate layer with the plurality of nano-features on the patterned region is carried out utilizing a sputtering process.

12. The method according to claim 1, wherein depositing the Au/Ti bilayer on the substrate layer with the nano-roughened patterned region comprises:
  depositing a Ti layer with a thickness between 3 nm and 10 nm on the substrate layer with the nano-roughened patterned region utilizing a sputtering process; and
  depositing an Au layer with a thickness between 10 nm and 50 nm on the deposited Ti layer utilizing a sputtering process.

13. The method according to claim 12, wherein depositing the Au/Ti bilayer on the substrate layer with the nano-roughened patterned region further comprises electrically passivating an area of the Au/Ti bilayer except the array of microelectrodes and the array of electrical connections.

14. The method according to claim 12, wherein depositing the Au/Ti bilayer on the substrate layer with the nano-roughened patterned region further comprises removing the Au/Ti bilayer except the array of microelectrodes and the array of electrical connections.

15. The method according to claim 1, wherein forcing the attachment between the at least one HUVEC and the at least one microelectrode of the array of microelectrodes on the biosensor comprises applying an electrically active positioning system to adhere the at least one HUVEC on the at least one microelectrode of the array of microelectrodes utilizing a dielectrophoresis (DEP) technique.

16. The method of claim 1, wherein stripping the photoresist layer from the substrate layer comprises removing the photoresist layer from the substrate layer by dissolving the photoresist layer in a solvent.

17. The method of claim 1, further comprising depositing an electrically insulator layer on a surface of the biosensor except for on a surface of the array of microelectrodes.

* * * * *